(12) United States Patent
Hayashi et al.

(10) Patent No.: US 8,179,524 B2
(45) Date of Patent: May 15, 2012

(54) HARD DISK INSPECTION APPARATUS

(75) Inventors: Yoichi Hayashi, Odawara (JP);
Shinichiro Okada, Odawara (JP)

(73) Assignee: Fujifilm Corporation, Tokyo (JP)

( * ) Notice: Subject to any disclaimer, the term of this patent is extended or adjusted under 35 U.S.C. 154(b) by 446 days.

(21) Appl. No.: 12/545,991

(22) Filed: Aug. 24, 2009

(65) Prior Publication Data

US 2010/0053602 A1 Mar. 4, 2010

(30) Foreign Application Priority Data

Aug. 29, 2008 (JP) ................................. 2008-222165

(51) Int. Cl.
*G01N 21/00* (2006.01)
*G01N 21/55* (2006.01)
*G01B 11/24* (2006.01)
*G01B 11/30* (2006.01)

(52) U.S. Cl. ....................... 356/237.2; 356/448; 356/601

(58) Field of Classification Search .... 356/237.1–241.6, 356/242.1–243.8, 426–431, 600–640
See application file for complete search history.

(56) References Cited

U.S. PATENT DOCUMENTS 4,423,331 A * 12/1983 Koizumi et al. ......... 250/559.45
6,057,926 A *  5/2000 Horai ............................ 356/430

FOREIGN PATENT DOCUMENTS

| JP | 6-148088 | 5/1994 |
| JP | 2000-9453 | 1/2000 |
| JP | 2000-162146 | 6/2000 |

* cited by examiner

*Primary Examiner* — Gregory J Toatley
*Assistant Examiner* — Jarreas C Underwood
(74) *Attorney, Agent, or Firm* — Young & Thompson

(57) ABSTRACT

A hard disk inspection apparatus comprises a disk holding device which holds a hard disk; a light source which generates a light that illuminates an inspection region portion of a hard disk that is held by the disk holding device; a light guide which has a branched shape and guides a light from the light source to a plurality of light projecting parts; and an image pickup device which takes an image by receiving reflected light from the inspection region portion; wherein an illumination light is shone onto the inspection region from plural courses by shining the illumination light that is guided by the light guide onto the inspection region front the plurality of light projecting parts.

4 Claims, 29 Drawing Sheets

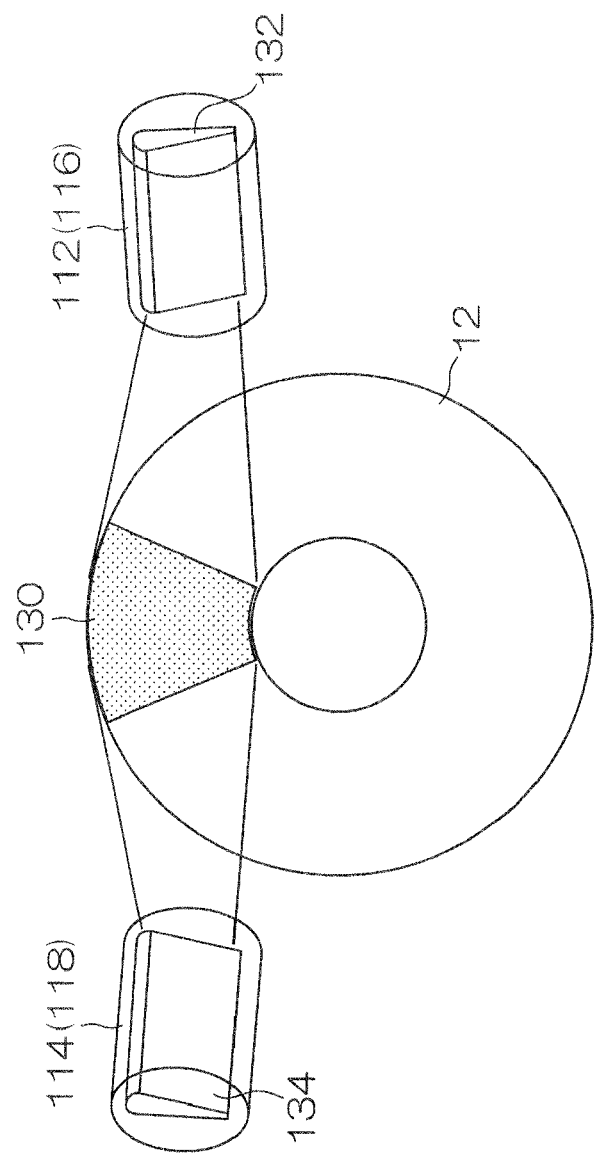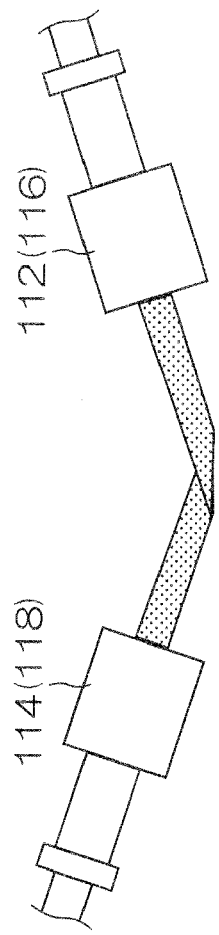

HARD DISK INSPECTION APPARATUS

BACKGROUND OF THE INVENTION

1. Field of the Invention

The present invention relates to a hard disk inspection apparatus that is suitable for inspecting a contamination state of a surface and an end face of a magnetic disk that is used for a hard disk apparatus.

2. Description of the Related Art

In recent years, recording densities of hard disk apparatus are being enhanced more and more, and head floating amounts are also becoming increasingly smaller. Consequently, not only are drop-outs caused by even minute particles, there is also an increased risk of particles becoming engaged with a head and damaging data. There is also a risk that the aforementioned damage may be caused by particles also moving to an inner circumferential face or an outer circumferential face of a disk, and not just to the recording surface. In particular, it is not possible to prevent an edge portion of a disk from contacting with a carrying case or a zip of a handling tool or equipment or the like, and an edge portion is also a source of particle generation because it has a corner. Because such particles move easily, they are liable to be the cause of a failure.

Further, according to magnetic transfer technology that previously writes information such as a servo signal onto a magnetic disk, it is necessary to bring a master disk (transfer source disk) and a slave disk (magnetic disk for transferring to) into close contact. However, a transfer fault arises when there is dust between the disks. Some of that dust is generated when manufacturing or transporting a slave disk, and which then adheres to and is introduced with the relevant slave disk. For dust that adheres to a disk in this manner, it is desirable that an inspection to determine the existence of dust is performed prior to such a transfer step, and that the dust is removed from a disk to which the dust adheres.

Conventionally, a magnetic disk that is used in a hard disk apparatus is inspected for the existence of defects or the adherence of particles on the surfaces thereof in a manufacturing step, and an inspection apparatus that uses a laser (Japanese Patent Application Laid-Open No. 2000-9453) or an inspection apparatus that uses an image pickup camera such as a CCD are in practical use (Japanese Patent Application Laid-Open No. 2000-162146 and Japanese Patent Application Laid-Open No. 6-148088).

SUMMARY OF THE INVENTION

However, the contents of Japanese Patent Application Laid-Open No. 2000-9453 relate to an inspection machine used exclusively for an end face that inspects only an outer circumferential end face (edge) of a hard disk. According to the apparatus disclosed in Japanese Patent Application Laid-Open No. 2000-9453, it is not possible to inspect an interior surface and an inner circumferential end face of a disk. In order to inspect an interior surface and an inner circumferential end face (edge) of a disk, it is necessary to provide respectively different inspection machines. Further, the technology described in Japanese Patent Application Laid-Open No. 2000-9453 is technology that measures the intensity in a specular direction of a laser beam shone onto a disk end face and the intensity of a diffuse reflection at an interior surface of a dividing and reflecting body. However, because the separation made between defects that have a small influence on failures, such as flaws at the disk end face, and dust (dust that has a large influence on failures) based on the relevant measurement information is insufficient, and furthermore, because the measurement principles of the relevant technology do not enable the obtainment of an image in which the state of an edge part is reflected, an inspection based on the measurement results is difficult.

In contrast, the apparatuses disclosed in Japanese Patent Application Laid-Open No. 2000-162146 and Japanese Patent Application Laid-Open No. 6-148088 inspect only a flat part (interior recording surface) of one side of a disk, and can not inspect an edge or the vicinity of an edge.

According to any of the apparatuses disclosed in the above described Japanese Patent Application Laid-Open Nos. 2000-9453, 2000-162146 and 6-148088, it is not possible to inspect the interior surface and an edge part of a disk simultaneously, and it is also not possible to simultaneously inspect both sides of a disk and an end face with a single machine. Assuming that a user attempts to inspect both sides of a disk, it is necessary for the user to combine two or more apparatuses and then turn over the disk to perform an inspection of the rear surface. Thus, the cost of the equipment is high and the size of the equipment increases, and it is necessary to provide an adequate installation location. Further, since it is necessary to turnover the disk repeatedly when inspecting an individual disk, particles are generated by such handling of the disk. This leads to a deterioration in quality and is also a major problem in terms of throughput.

Further, in an optical inspection in which an illumination light is shone on an inspection surface of a disk to pick up an image of the reflected light thereof, it is important to make the amount of illumination light stable and uniform.

The present invention has been made in view of the above described circumstances, and an object of the invention is to provide a hard disk inspection apparatus that can stabilize and uniformize an amount of illumination light with respect to an inspection target region of a hard disk and that is also favorably applied to simultaneous inspection of a surface (recording surface portion) and an end face (edge part) of a disk or to simultaneous inspection of both sides of a disk.

To achieve the aforementioned object, a hard disk inspection apparatus according to the present invention comprises a disk holding device which holds a hard disk; a light source which generates a light that illuminates an inspection region portion of a hard disk that is held by the disk holding device; a light guide which has a branched shape that guides a light from the light source to a plurality of light projecting parts; and an image pickup device which picks up an image of reflected light from the inspection region portion; wherein an illumination light is shone onto the inspection region from a plurality of directions by shining a light that is guided by the light guide onto the inspection region from the plurality of light projecting parts.

According to the present invention, it is possible to maintain a stable balance among the light amounts of illumination light emitted from a plurality of light projecting parts that illuminate the same inspection surface. Even in a case in which changes in the light amounts occur due to deterioration of a light source or the like, the light amount balance is maintained.

A hard disk inspection apparatus according to one aspect of the present invention, the light source and the light guide are provided for each of a first inspection surface that is a surface of one side of the hard disk and a second inspection surface that is a surface of another side of the hard disk.

According to the aspect which simultaneously inspects two sides of a disk, a configuration comprising one light source for one inspection surface is preferable.

As another aspect of the present invention, there is provided the hard disk inspection apparatus, wherein the light projecting parts illuminate an illumination light of an illumination light pattern that, with respect to an inspection region portion of a predetermined shape of a disk surface that includes an edge of a disk held by the disk holding device, becomes an irradiation range that has a shape that is approximately the same as the shape of the inspection region.

According to the above aspect, it is possible to simultaneously inspect a flat part and an edge portion of a disk. In particular, since the illumination device of the present invention performs pattern illumination has an irradiation range that approximately matches the shape of an inspection region, abnormal reflection or blooming at an edge part can be prevented and unwanted imprinting can also be suppressed.

According to the present invention, illumination light for which a light amount balance is stabilized can be illuminated onto a hard disk that is an object for inspection, and a contamination state (adherence of dust or the like) of the disk can be inspected with a high accuracy based on a picked-up image that captures a reflected light.

BRIEF DESCRIPTION OF THE DRAWINGS

FIGS. 13A and 13B are explanatory views of an illumination apparatus that is used in the disk inspection apparatus;

DETAILED DESCRIPTION OF THE PREFERRED EMBODIMENTS

Hereunder, a preferred embodiment of the present invention is described in detail in accordance with the attached drawings.

First, the configuration of a chucking apparatus for a disk that is used in a hard disk inspection apparatus according to an embodiment of the present invention is described in this connection, the present embodiment is described by taking as an example a disk inspection apparatus as well as a chucking apparatus for a magnetic disk that is used in a hard disk apparatus.

[Configuration Example of Disk-Chucking Apparatus]

Figure 1:
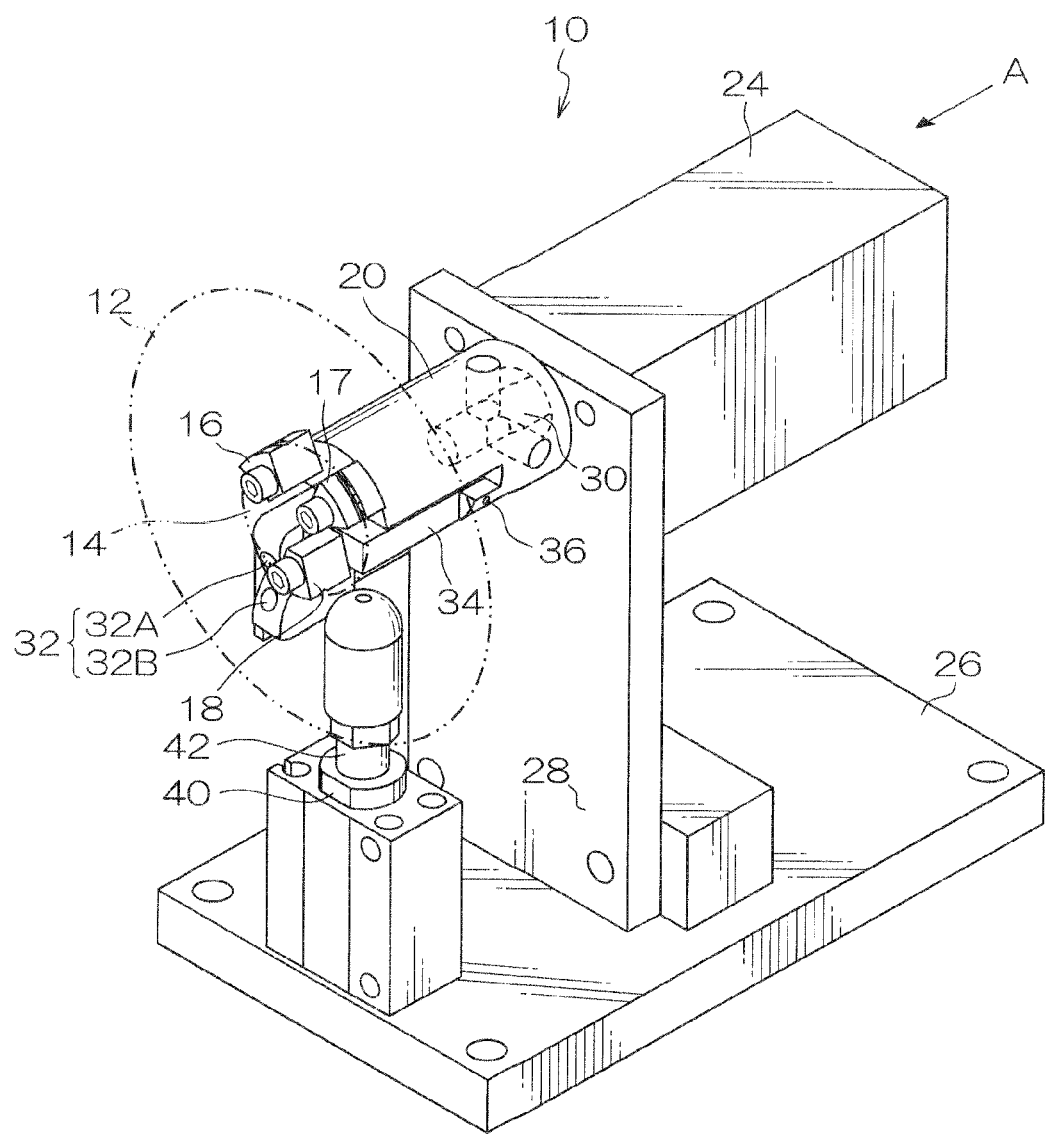
FIG. 1 is an oblique perspective view of a chucking apparatus according to an embodiment of the present invention.
Figure 2:
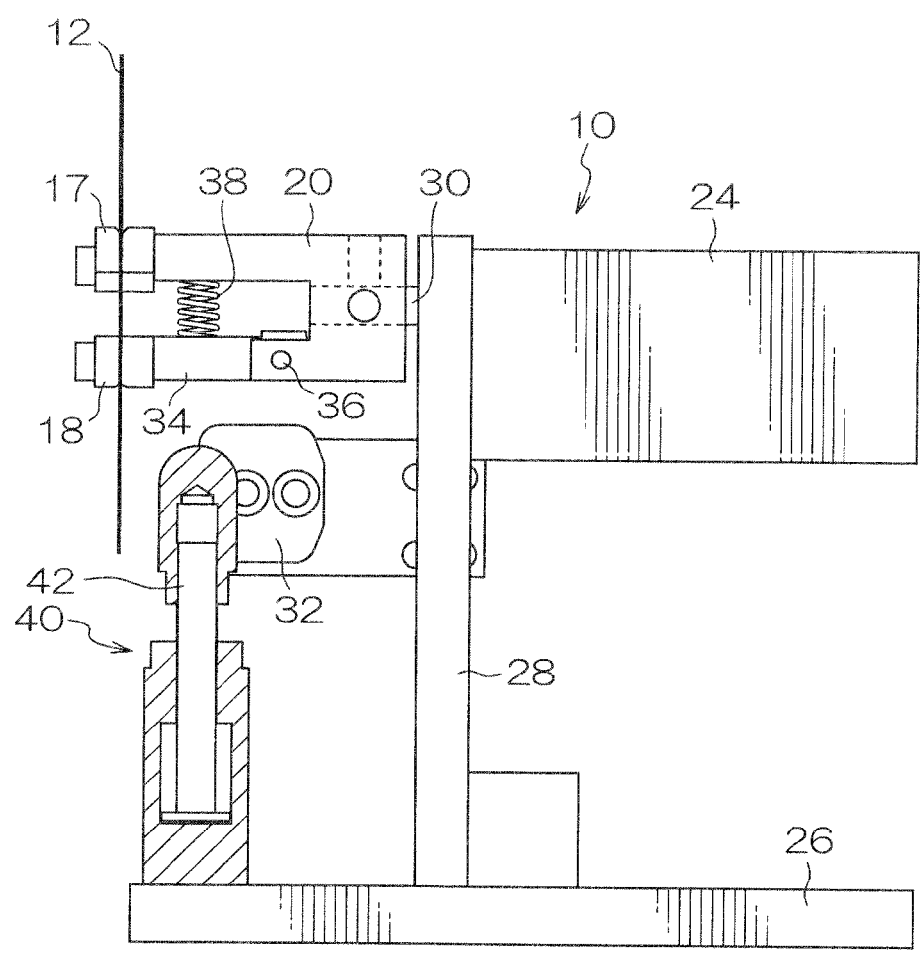
FIG. 2 is a lateral view of the chucking apparatus shown in FIG. 1.

FIG. 1 is an oblique perspective view that shows a configuration example of a disk-chucking apparatus that is used in a hard disk inspection apparatus according to an embodiment of the present invention, and FIG. 2 is a lateral view thereof. A chucking apparatus 10 according to the present embodiment shown in these drawings includes a chuck main body 20 that has three claws 16, 17 and 18 that contact with an edge (disk inner circumferential face) of a hole 14 that is formed in a center part of a disk 12, and a motor 24 that rotates the chuck main body 20.

The motor 24 is fixed to a supporting plate 28 that stands in a perpendicular condition with respect to the base plate 26. A rotating shaft (spindle 30) of the motor 24 faces in a horizontal direction (direction orthogonal to the direction of gravity). The chuck main body 20 that is mounted to the distal end of the spindle 30 holds the disk 12 in an vertically upright posture (posture in which the surface of the disk is parallel with the direction of gravity) using the three claws 16, 17, and 18.

A non-contact distance sensor 32 is mounted to the supporting plate 28. The position of the surface of the disk 12 is detected by the distance sensor 32. Based on a detection signal of the distance sensor 32, it is possible to determine whether or not the disk 12 is held in a correct position (with a correct posture). In this connection, although the optical distance sensor 32 that has a light projecting part 32A that emits a laser beam and a light receiving part 32B that receives reflected light from an object to be measured is used according to the present example, the distance sensor is not limited to an optical distance sensor, and the distance sensor may be in accordance with another system such as an ultrasound system.

Among the three claws provided in the chuck main body 20, two claws designated by reference numerals 16 and 17 (two claws arranged side by side at the upper part in FIG. 1) are fixed claws, and the remaining claw designated by reference numeral 18 (claw arranged at the lower part in FIG. 1) is a movable claw. Hereunder, the claws designated by reference numerals 16 and 17 may be referred to as "fixed claw" and the claw designated by reference numeral 18 may be referred to as "movable claw".

A proximal end portion of an arm 34 of the movable claw 18 is attached to the chuck main body 20 through a rotating shaft 36. The arm 34 of the movable claw 18 is urged downward (in a direction which spreads the movable claw 18 in the diametrical direction of the hole 14) in FIG. 2 by a spring member (corresponds to "urging device"; although a helical compression spring is used according to the present example, a magnetic, air pressure, or plate spring or the like can also be used) 38. In a state in which an external force is not applied, the movable claw 18 is supported approximately horizontally, similarly to the fixed claws 16 and 17. In actuality, because a chucking margin is required, the movable claw 18 is inclined to a certain extent, and has an inclination of about 0.1 mm to 0.5 mm with regard to the distance from a horizontal position.

Figure 3:
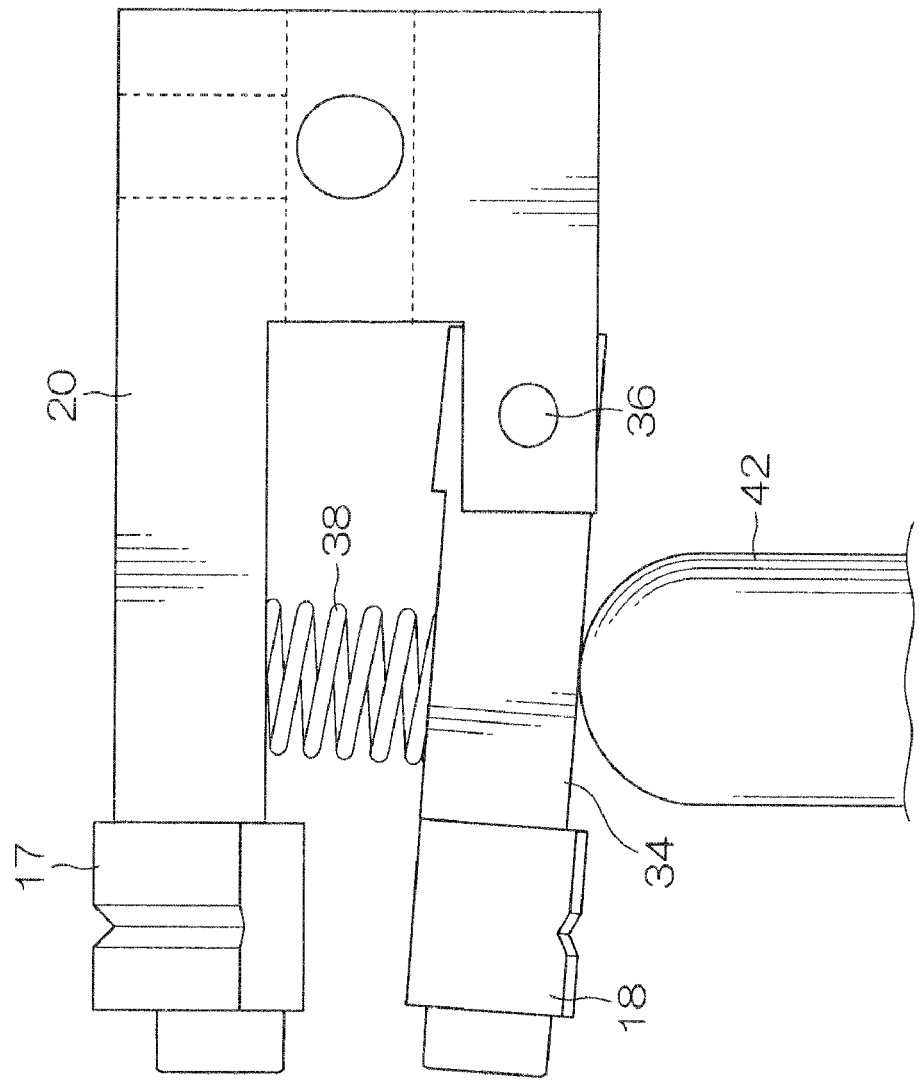
FIG. 3 is an enlarged view of principal parts that shows a drive mechanism of a movable claw.

A cylinder 40 (corresponds to "claw driving device") as a device which pushes up the movable claw 18 is arranged on the underside of the arm 34 of the movable claw 18. By extending a rod 42 of the cylinder 40, the arm 34 of the movable claw 18 can be pushed upward against an urging force of the spring member 38 (see FIG. 3). When the rod 42 is retracted from this state, the movable claw 18 returns to the original horizontal position thereof due to a restoring force of the spring member 38. A driving device which causes the movable claw 18 to change position against the urging force of the spring member 38 is not limited to the aforementioned cylinder 40, and may be another device that employs an actuator or compressed air.

Because a portion of the rotating shaft 36 (corresponds to "sliding portion of movable mechanism") which oscillatably supports the movable claw 18 is a sliding portion at which members rub against each other, in consideration of generation of particles caused by the sliding of members, a configuration in which the relevant sliding portion is arranged at a position that is adequately separated from the disk 12 is preferable. As a design guideline, it is desirable that a distance from the disk 12 to the sliding portion is such that the sliding portion is provided at a position that is separated by an amount of the (outer circumferential radius—inner circumferential radius) of the disk 12 or more from the disk 12, and it is more desirable that the sliding portion be provided at a position that is separated from the disk 12 by the amount of the outer circumferential radius of the disk 12 or more.

Although the movable claw 18 is oscillatingly moved by an arcuate motion that centers on the rotating shaft 36, a mechanism that moves the movable claw 18 is not limited to that of the present example. For example, a mechanism may also be used that moves the movable claw by a linear motion.

However, since the sliding portion becomes significantly complex when using a mechanism that employs a linear motion in comparison to an arcuate motion, unless there is a restriction on the positional accuracy, a mechanism employing arcuate motion as in the present example has a simpler structure and also facilitates the suppression of particle generation.

Figure 4:
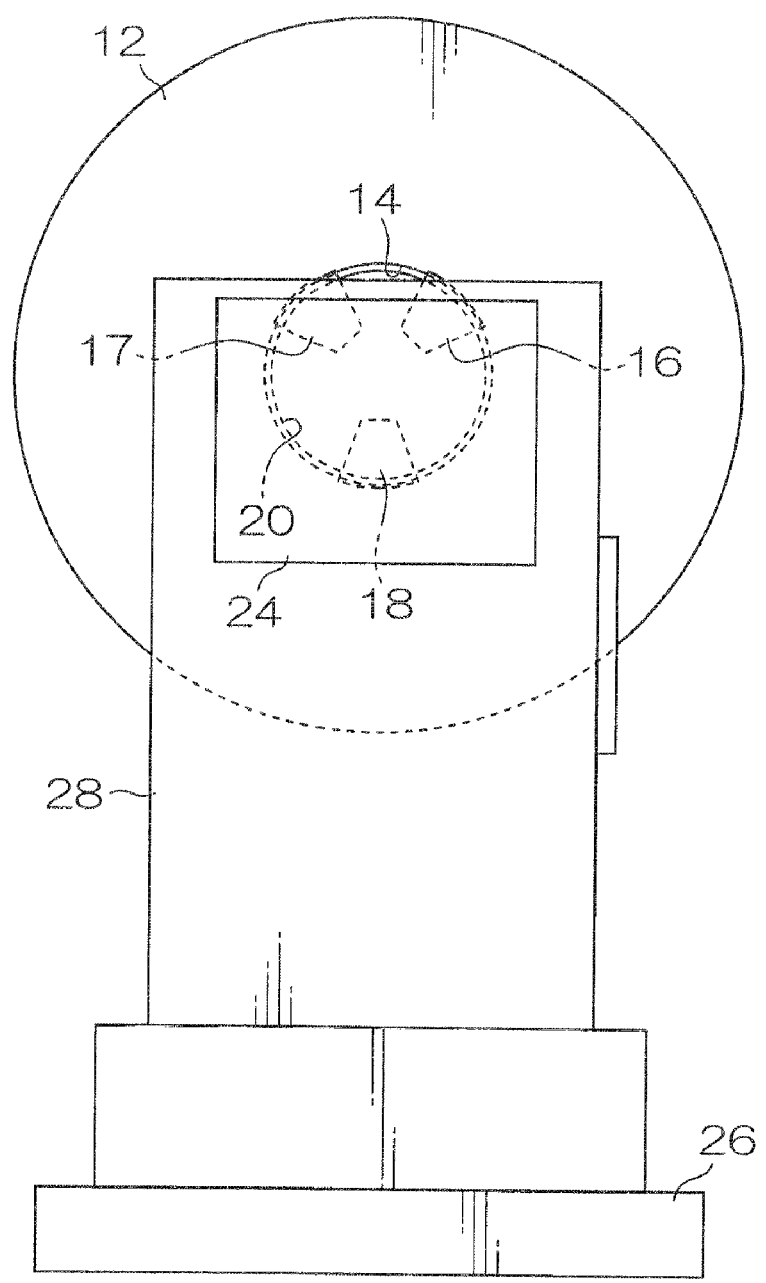
FIG. 4 is a rear view of the chucking apparatus shown in FIG. 1.

FIG. 4 is a rear view (view from the arrow A direction in FIG. 1) of the chucking apparatus 10. The outer diameter of the chuck main body 20 is less than or equal to the diameter of the hole 14 of the disk 12 (preferably, less than the hole diameter), and the three claws 16, 17, and 18 are also arranged so as to fit as much as possible on the inner side of the hole diameter of the disk 12.

The height of the upper end face of the supporting plate 28 is arranged so as to be equal to or less than the height of the chuck main body 20 (see FIG. 2), and the motor 24 that is fixed to the supporting plate 28 is also arranged so as not to exceed the height of the upper end face of the supporting plate 28. The configuration is realized by shifting a shaft of the motor using a gear or pulley, or by using a motor with a small diameter.

According to this configuration, as shown in FIG. 4, when viewed from a perpendicular direction with respect to the recording surface of the chucked disk 12, almost the entire area in a diametrical direction can be observed without an obstacle on both sides with respect to one part (upper region in FIG. 4) of the disk 12. In the case of the present example, a region that includes at least a recording surface region (designated by reference numeral 130 in FIG. 13A) of a predetermined angle range ($\alpha=45°$) as an inspection range in a disk inspection apparatus described later (FIG. 10) can be observed without an obstacle. It is therefore possible to perform a two-sided simultaneous inspection using a disk inspection apparatus. Further, an inspection can be performed as far as a region that is extremely close to the inner circumferential edge of the disk.

Figure 5:
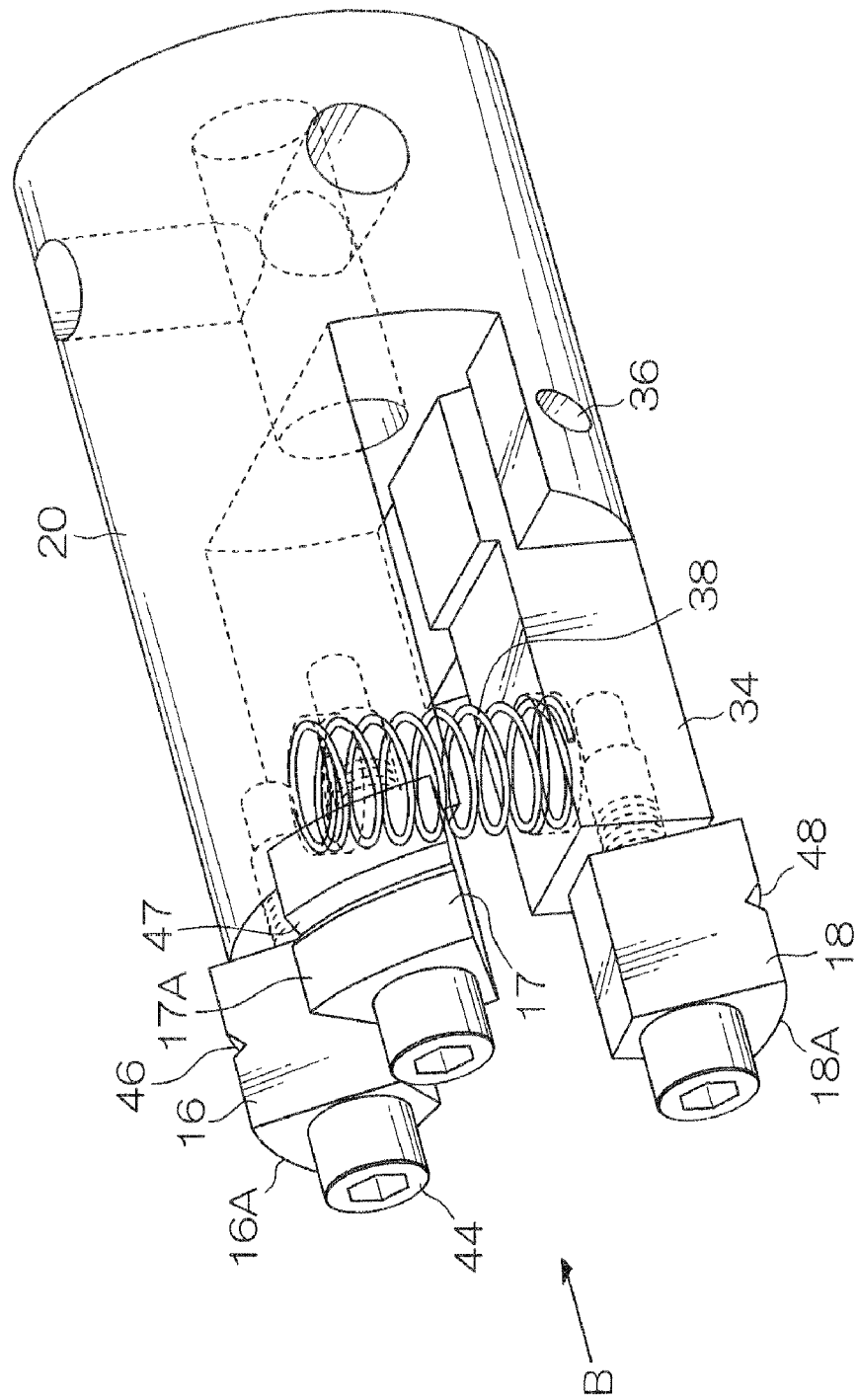
FIG. 5 is an oblique perspective view of the chuck main body.

FIG. 5 is an oblique perspective view of principal parts of the chucking apparatus 10. As shown in FIG. 5, each of the claws 16, 17, and 18 is manufactured as a separate member to the chuck main body 20 using a separate material, and is fixed to the chuck main body 20 by a bolt 44.

Polybenzimidazole (PBI) is suitable as the claw material to be used for the fixed claws 16 and 17 and the movable claw 18. Polybenzimidazole has a high level of abrasion resistance and slidability with respect to a disk, particularly a glass disk, and generates almost no particles. There is also the advantage that polybenzimidazole has exhibits low reflectivity with no additives, and it is thus possible to avoid influencing an inspection for particle adherence (optical inspection that performs illumination with a high illuminance) that is described later. Although a method exists in which carbon is added to a resin in order to obtain low reflectivity, from the viewpoint of particle suppression, use of an additive-free material is preferable.

A configuration in which each of the claws 16, 17, and 18 is formed in a shape that contacts only with the inside edge of the hole of the disk 12 in a chucked state, and does not contact with the flat surface (recording surface) of the disk is desirable. The claws 16, 17, and 18 of the present example have outside edges 16A, 17A, and 18A that are partially arc shaped along the inner circumference of the hole of the disk 12. Grooves 46, 47, and 48 that contact against the circumferential edge of the hole 14 of the disk 12 are formed in the arc-shaped outside edges 16A, 17A, and 18A of the claws 16, 17, and 18, respectively. The holding position and posture of the disk 12 is regulated by the grooves 46, 47, and 48.

Figure 6:
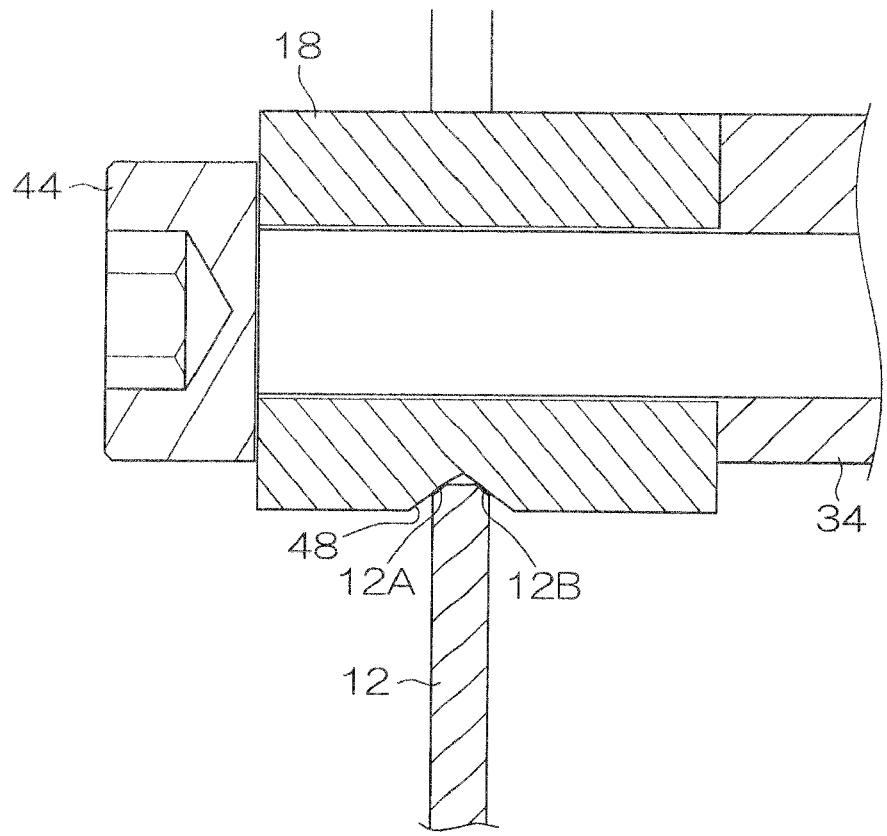
FIG. 6 is an enlarged view of a movable claw portion at a time of chucking.

FIG. 6 is an enlarged view of the groove 48 formed in the movable claw 18. In this connection, since the grooves 46 and 47 are similarly formed in the fixed claws 16 and 17, the description of the groove 48 of the movable claw 18 shown in FIG. 6 is representative of the description for the grooves 46 and 47.

As shown in FIG. 6, the groove 48 has a V-shaped cross section. The angle of the sloping surface of the V shape matches the chamfering angle of the inner circumferential edge of the disk 12. At the time of chucking, chamfered faces 12A and 12B of the inner circumferential edge of the disk 12 contact with the groove 48, and the claw 18 is pushed against with the urging force of the spring member 38 so that the disk 12 is held. Although a deep groove 48 is depicted in FIG. 6 to facilitate the description, because a portion (region that can not be inspected) that is concealed by the groove among the flat part (recording surface region) of the disk increases if the groove 48 is made too deep, it is better that the groove 48 is made as shallow as possible.

Figure 7:
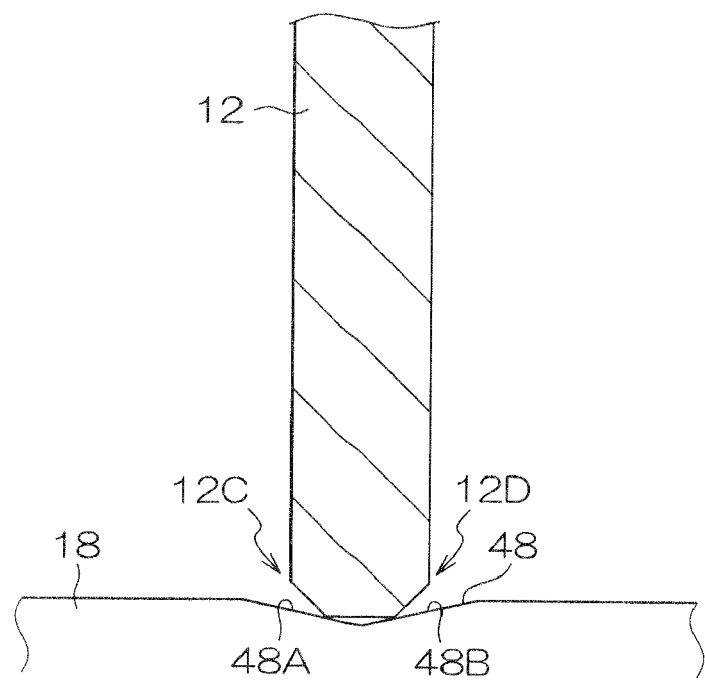
FIG. 7 is a view showing another example of the form of a groove that is formed in an outside edge of a claw.

The form of the groove 48 is not limited to the example shown in FIG. 6. For example, as shown in FIG. 7, a form of an extremely shallow groove in which an angle of inclination of the inclined surfaces of the groove 48 is extremely small and a spreading angle formed between inclined surfaces 48A and 48B that face each other is large is also preferable. By adopting this form, it is possible to inspect as far as corner parts (reference numerals 12C and 12D) of the recording surface of the disk 12, and thus adherence of dust at the corner part 12C can be inspected.

In this connection, if the positioning accuracy of disk handling performed by a handling robot (unshown) is improved, it is also possible to omit the groove 48.

Figure 8:
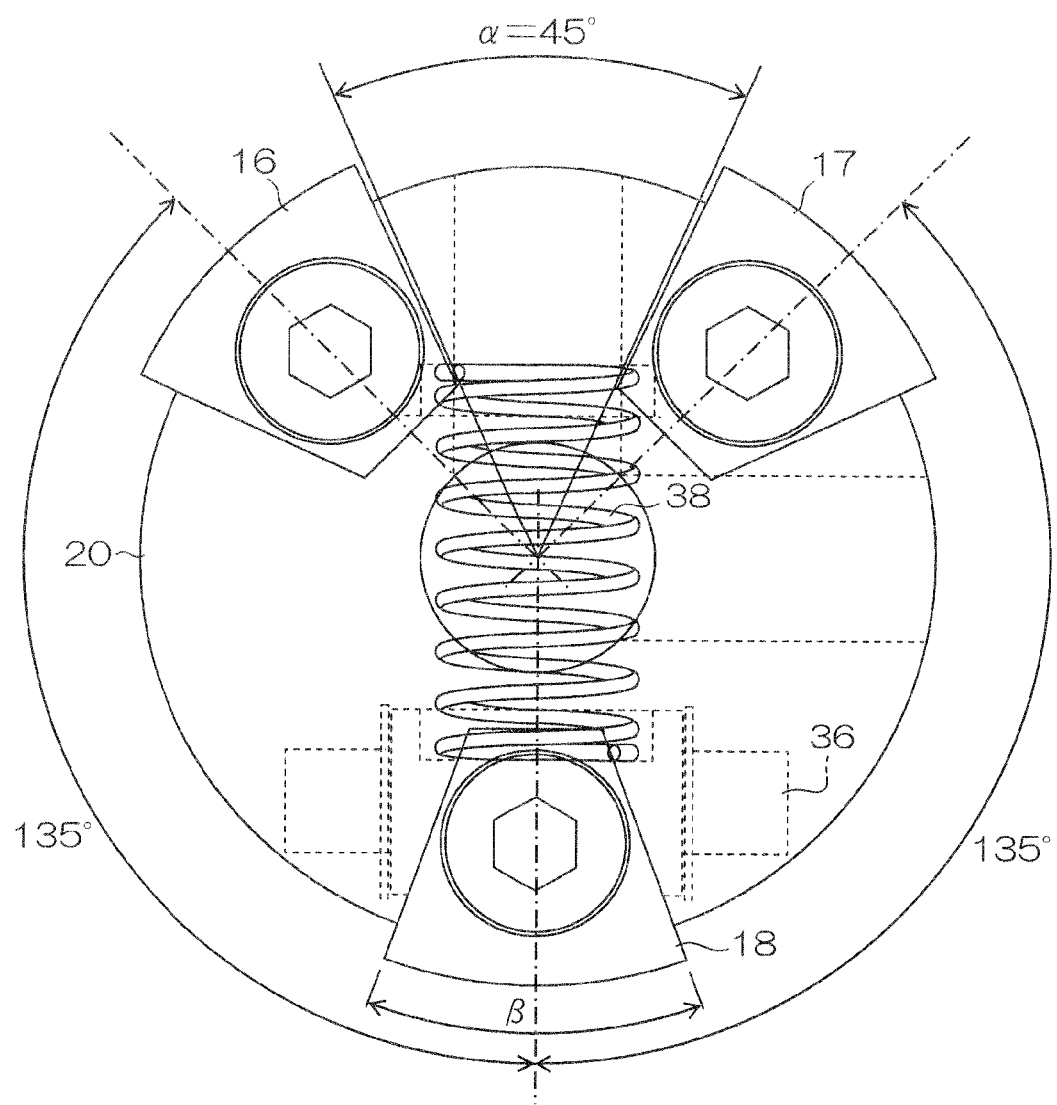
FIG. 8 is a view from the direction of an arrow B in FIG. 5.

FIG. 8 is a front elevation view of the chuck main body 20 (view as seen from the direction of the arrow B in FIG. 5). The positional relationship between the fixed claws 16 and 17 and the movable claw 18 is as shown in FIG. 8. More specifically, the three claws 16, 17, and 18 are disposed on the same circumference that takes the center of the spindle 30 as an origin. The fixed claw 17 is disposed at a position that is rotated by 135 degrees in the counter-clockwise direction from the movable claw 18 that is arranged at the lowermost position (position equivalent to 6 o'clock on a watch) in FIG. 8. The fixed claw 16 is disposed at a position that is rotated by 135 degrees in the clockwise direction from the movable claw 18.

More specifically, an angle $\theta 1$ between the positions of the two fixed claws 16 and 17 around the center of the spindle 30 is 90 degrees, and an angle $\theta 2$ between the position of the movable claw 18 and the position of the fixed claw 16 (or 17) around the center is 135 degrees. In this connection, taking into consideration the stability and the like when mounting a disk, $\theta 1 < \theta 2$ is preferable.

The arrangement of claws described in the present example is suitable for a case in which a disk inspection apparatus, described later, is used to perform an inspection of the entire area of the surface of a single disk 12 over eight separate times by inspecting a 45 degree region of the disk surface each time. There is also the advantage that the disk 12 in a vertical posture can be held stably.

On the flat surface as seen from the arrow B direction as shown in FIG. 8, the respective claws 16, 17, and 18 are formed in an approximately fan shape. Preferably, an angle $\beta$ with respect to the center of an arc (arc of the outside edge) of each of the claws 16, 17, and 18 is made a slightly smaller angle (in the present example, 43 degrees) than the angle $\alpha$ (in the present example, $\alpha = 45$ degrees) of a single inspection range. The dispositional arrangement of the fixed claws 16 and 17 and the movable claw 18 and an angle with respect to the center of the arc of each of the claws 16, 17, and 18 are not limited to the present example, and are decided based on the angle $\alpha$ of an inspection range for one time regarding an inspection by the disk inspection apparatus and in consideration of disk holding stability.

Further, although a claw arrangement comprising the two fixed claws 16 and 17 and the single movable claw 18 is given as an example according to the present embodiment, various configurations are possible with respect to the number and arrangement of claws, the ratio of number of movable claws to number of fixed claws, and the dispositional balance and the like.

The operations when the disk 12 is chucked by the chucking apparatus 10 configured as described above are as follows.

Handling of the disk 12 is performed by an unshown handling robot. The handling robot grasps the disk 12 with a plurality of claws, and carries the disk 12 to the chucking apparatus 10.

Although the mechanism for holding the disk 12 with the handling robot is not particularly limited, for example, a configuration is adopted that supports the outer circumference of the disk 12 with three claws by employing a claw structure (two fixed claws and one movable claw) resembling that of the chucking apparatus 10 of the present example for outer circumferential chucking. In this connection, since the chucking apparatus 10 of the present example is in accordance with an inner circumferential chucking method, it is convenient that the handling robot employs an outer circumferential chucking method. However, a configuration may be adopted that employs an inner circumferential chucking method for the handling robot also, and with which delivery of the disk 12 is performed by the chucking apparatus 10 utilizing the gaps between the claws 16, 17, and 18.

In order that an operation to transport the disk 12 by the handling robot and an operation by the cylinder 40 of the chucking apparatus 10 are performed at the proper timing, a configuration in which the robot side controls the cylinder 40 is desirable. More specifically, a configuration is adopted in which the cylinder 40 is also controlled by a control apparatus that controls the handling robot. When mounting the disk 12 to the chucking apparatus 10, first, the rod 42 of the cylinder 40 is extended to push the movable claw 18 upward (see FIG. 3).

In this state, the handling robot approaches together with the disk 12, the hole 14 of the disk 12 is aligned with the position of the claws 16, 17, and 18, and the disk 12 is moved so that the claws 16, 17, and 18 are inserted into the hole 14 of the disk 12. After the disk 12 is moved as far as the position of the grooves 46 and 47, the disk 12 is lowered slightly so that the inside edge of the disk stops at a position at which the inside edge is on the verge of contact (distance of 0.1 mm or less therebetween) with the fixed claws 16 and 17. At this time, when the chucking of the handling robot is released, the disk 12 engages under its own weight with the fixed claws 16 and 17 without any strain.

Figure 9:
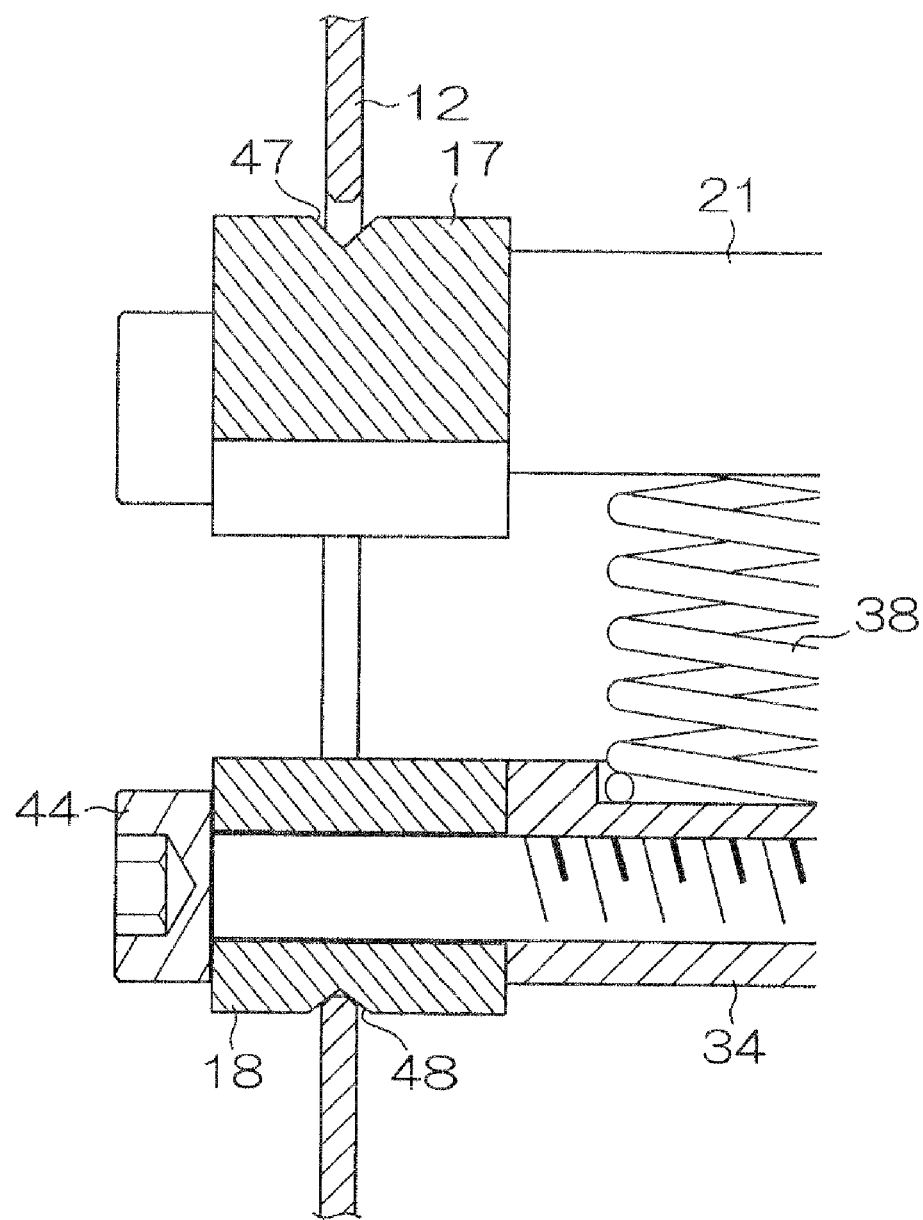
FIG. 9 is a cross section view that illustrates a chucked state of a disk.

Thereafter, the rod 42 of the cylinder 40 is gently lowered, the movable claw 18 is moved downward by the force of the spring member 38, and the movable claw 18 contacts against the inner circumference of the disk 12. Thus, by releasing the external force produced by the rod 42, the claws 16, 17, and 18 are brought into pressurized contact with the inner circumference of the disk 12 by the urging force of the spring member 38 so that the disk 12 is stably held. FIG. 9 shows a cross section of the principal parts in the chucked state.

In this connection, when demounting the disk 12 that is in a chucked state, operations that are the reverse of those at the time of mounting as described above are performed.

According to the chucking apparatus 10 of the present embodiment, the following operational advantages are obtained:

(1) The occurrence of flaws or particles can be suppressed;

(2) Simultaneous inspection of both sides of a disk is enabled, and a fast cycle time can be realized;

(3) The chucking apparatus can be made with a simple configuration;

(4) Inspection is possible as far as the vicinity of the inner circumferential edge of a disk;

(5) Because the disk 12 is held vertically, an air flow produced by a clean air flow from an upper direction is easily maintained in a laminar flow state, and since a turbulent flow does not arise at the rear of the disk, the adherence of particles can be significantly reduced;

(6) Because the disk 12 is held vertically, adherence of particles that drop down due to gravity from various machine structures (mechanical structures) that are arranged above the disk 12 can be avoided; and (7) By appropriately selecting the dispositional arrangement and the claw material of the claws 16, 17, and 18, the disk reception stability from the handling robot can be improved, and the occurrence of flaws or particles due to friction at the time of chucking can be suppressed.

[Description of Disk Inspection Apparatus]

Next, an example of a disk inspection apparatus (inspection apparatus for detecting dust adhered to a disk) that uses the above described chucking apparatus 10 is described.

Figure 10:
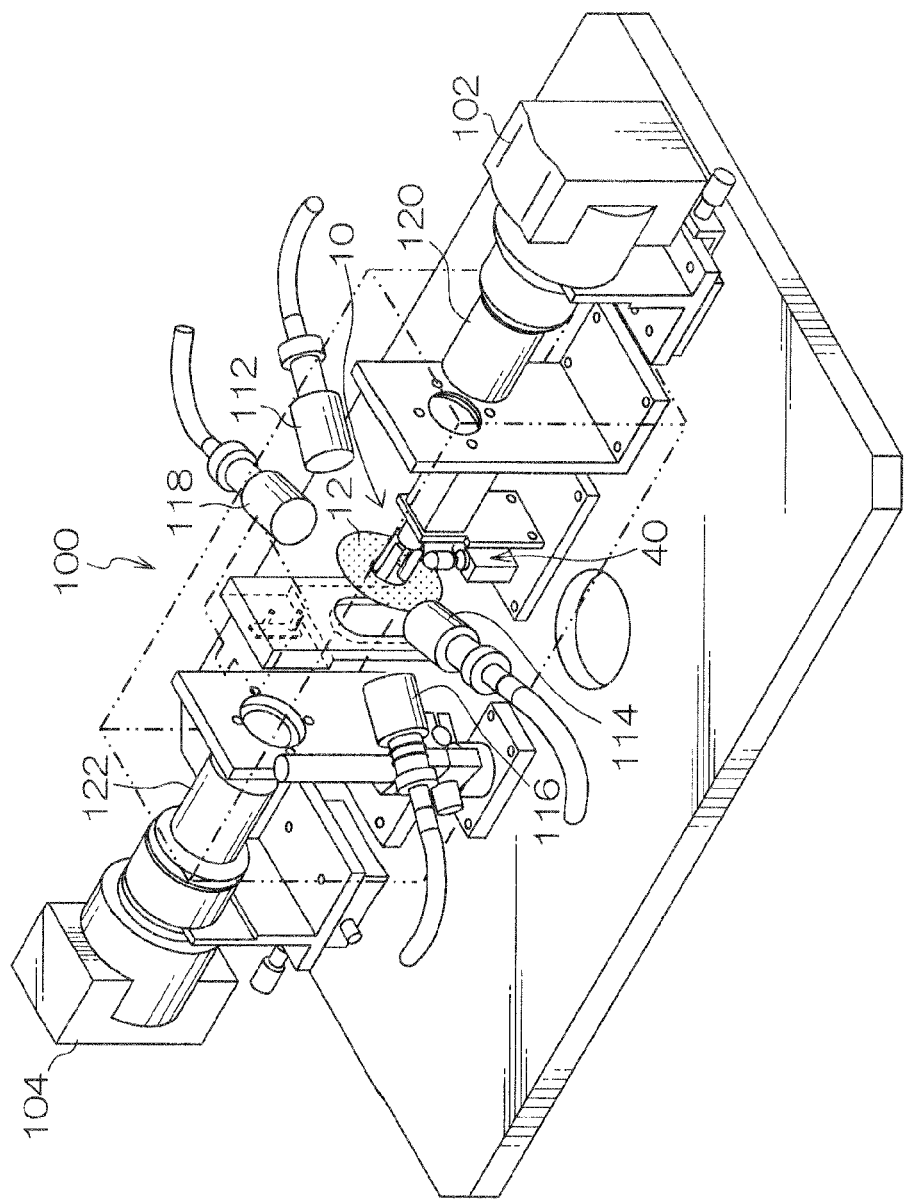
FIG. 10 is an oblique perspective view showing a configuration example of a disk inspection apparatus.
Figure 11:
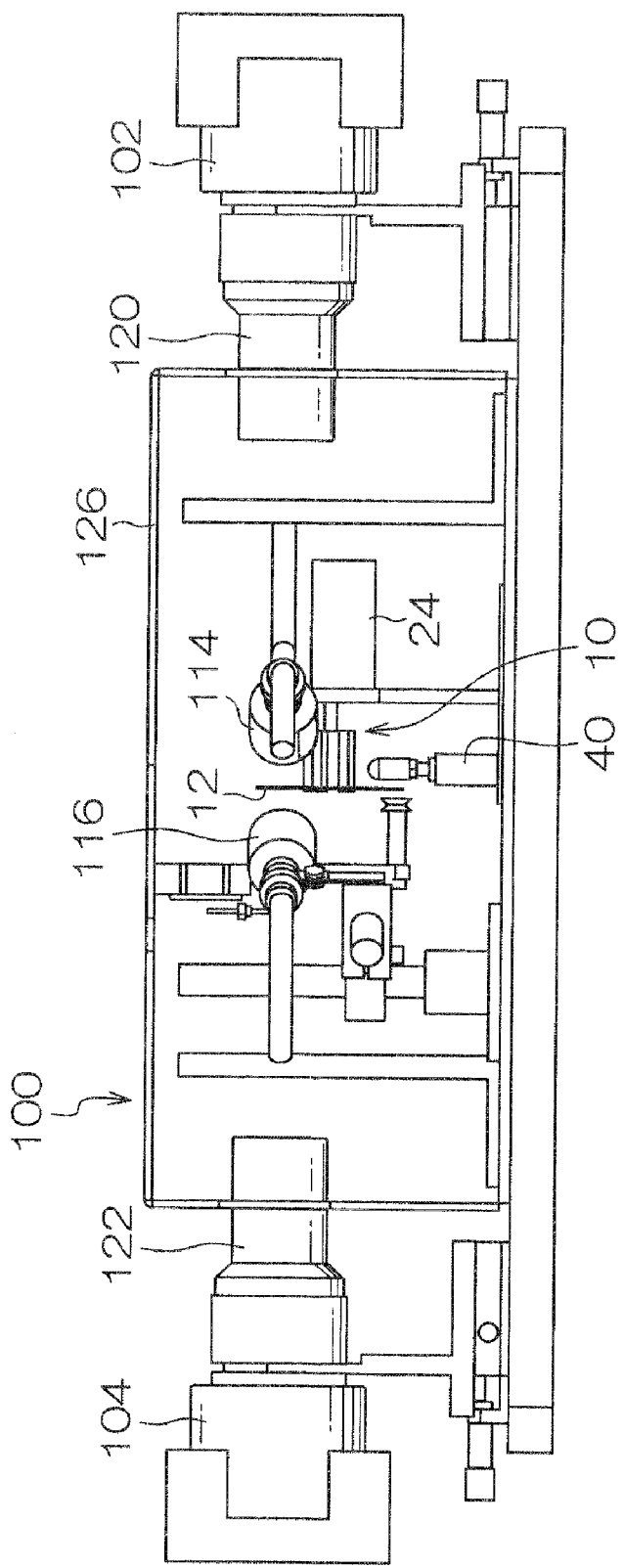
FIG. 11 is a lateral view of the disk inspection apparatus shown in FIG. 10.
Figure 12:
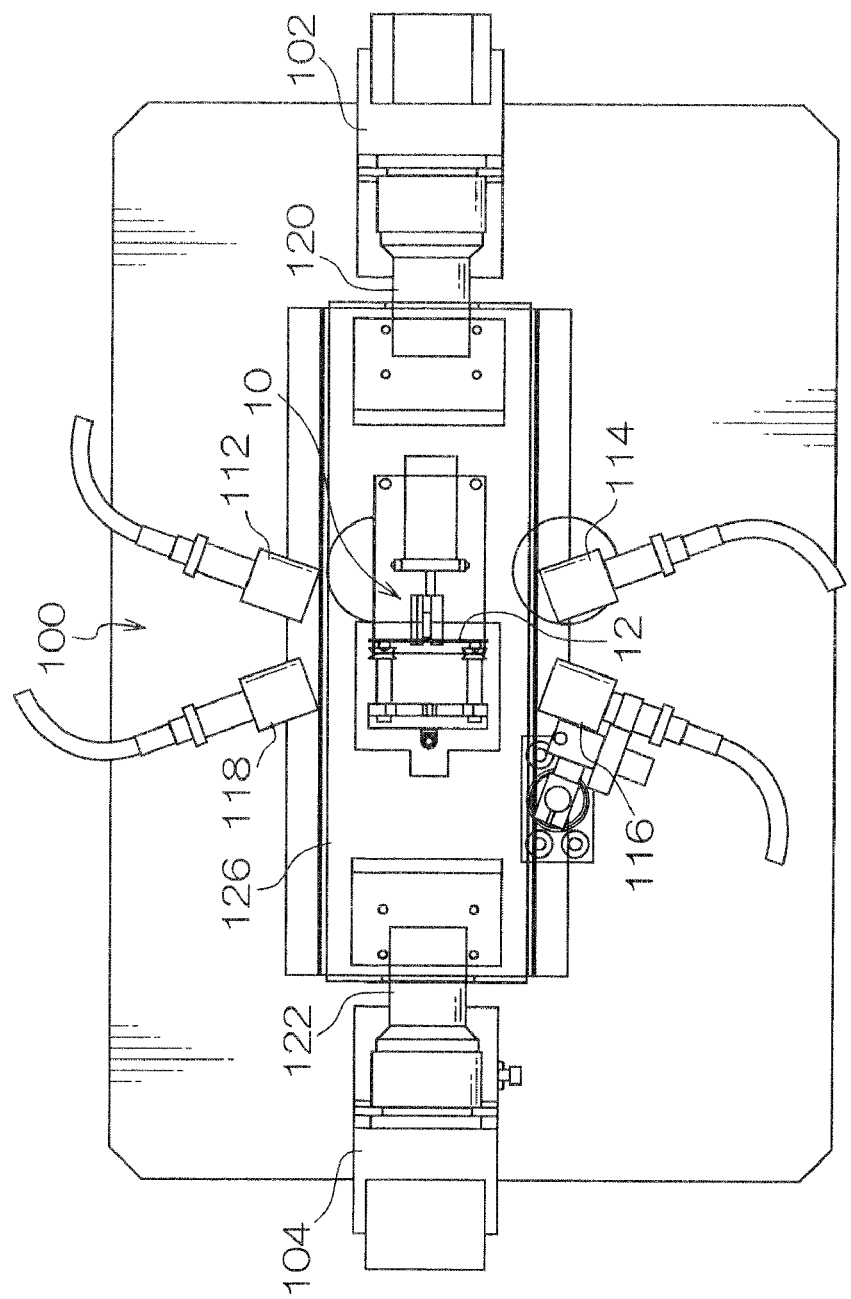
FIG. 12 is a plane view of the disk inspection apparatus shown in FIG. 10.

FIG. 10 is an oblique perspective view showing the configuration of a disk inspection apparatus according to an embodiment of the present invention, FIG. 11 is a lateral view of the disk inspection apparatus, and FIG. 12 is a plane view thereof. As shown in these drawings, in a disk inspection apparatus 100, a camera 102 (corresponds to "first imaging apparatus") and a camera 104 (corresponds to "second imaging apparatus") are disposed facing each other on two sides that sandwich the disk 12 that is held by the chucking apparatus 10, and illumination apparatuses 112, 114, 116, and 118 are disposed at somewhat diagonal positions in the lateral direction with respect to the disk 12. Reference numerals 120 and 122 designate a lens part of the cameras 102 and 104, respectively.

The pair comprising the illumination apparatuses 112 and 114 corresponds to a "first illumination device", and the pair comprising the illumination apparatuses 116 and 118 corresponds to a "second illumination device".

In this connection, the space surrounding the disk 12 as the inspection object is covered with a cover 126 during an inspection in order to prevent infiltration of disturbance light from the outside.

The cameras 102 and 104 are electronic imaging apparatuses that are provided with image pickup elements (CCD or CMOS or the like) that have a high resolution and a long charge storage time. According to the present example, an electrically cooled CCD camera is used. A CCD is preferable in the respect that a dark current noise thereof is less than that of a CMOS. Further, a noise component of a dark current can be reduced by cooling the CCD. Preferably, a cooling temperature is 10° C. or less. Although the dark current noise is reduced as the temperature decreases, when operation is performed for a long time, in some cases a problem arises due to freezing when a cooling temperature is 0 degrees or less, and hence the cooling temperature according to the present example is controlled to 1 degree. Preferably, a charge storage time is 0.1 seconds or more.

<Configuration of Illumination Apparatus>

As shown in FIG. 13A, the illumination apparatuses 112 to 118 are apparatuses that perform illumination with a pattern that matches a fan shape of an inspection range (disk upper region in 45 degree range with respect to the center) 130 of the disk 12. The illumination apparatuses 112 to 118 form an illumination pattern (fan-shaped pattern) using optic fibers (correspond to "light guides") 132 and 134 and projection lenses (unshown) at the distal ends thereof and perform pattern illumination from a diagonal position at a shallow angle with respect to a disk surface from the end faces of the optic fibers 132 and 134 of the light projecting parts (see FIG. 13B). Preferably, the elevation angle of an illumination light with respect to the disk surface is 30 degrees or less (60 degrees or more with respect to the angle of incidence), and in the present apparatus the elevation angle is taken as 20 degrees.

Since the disk 12 for a hard disk is a mirror surface, unless appropriate illumination is performed, reflection or blooming caused by the edge of the disk 12, imprinting to a disk surface (phenomenon whereby a camera lens or illumination light source is printed onto the disk 12 surface), or the like occurs, and it is difficult to perform a high accuracy inspection.

Therefore, according to the present embodiment, as shown in FIG. 13A, a white illumination light of an ultra-high brightness (for example, 1 million lux or more, more preferably 2 million lux or more) is shone only at the inspection range 130, so that by increasing the brightness of dust on the disk surface while also suppressing irradiation of light to unnecessary areas other than the inspection range 130, reflection of light by the chucking claws 16, 17, and 18 is suppressed, reflection or blooming by the edge of the disk 12 is suppressed, and imprinting to the disk surface is prevented. Accordingly, while a size and shape of the illumination light on the inspection range 130 being same size and shape of the inspection range 130 is preferable, size and shape variations of the illumination light on the inspection range 130 are allowable to the extent that above mentioned advantages are produced.

Generally, a large number of concentric, minute filaments (concavo-convex grooves) called "texture" are formed on the surface of the disk 12. According to the present embodiment, a configuration is adopted that shines an illumination light from the direction of the texture lines (direction of circumferential tangent) onto the disk 12. More specifically, the pair of illumination apparatuses 112 and 114 (or 116 and 118) are disposed so as to shine illumination light parallel to the tangential direction of the texture in the planar view shown in FIG. 13A.

Further, by performing illumination symmetrically from both sides with respect to the disk 12, the brightness inside the irradiation region (inside the illumination pattern) is also made uniform. In this connection, a metal halide lamp which uses few infrared rays and achieves a high light amount of 400 to 550 nm with a high resolution can be used as a high-brightness white-light source.

Figure 14:
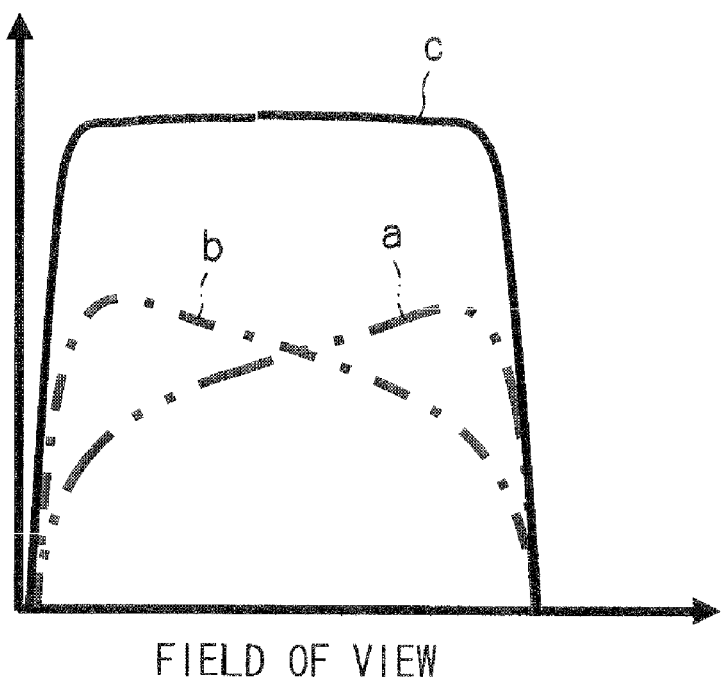
FIG. 14 is a view showing a luminance distribution of an illumination light pattern.

FIG. 14 is a view that illustrates the luminance distribution of an approximately fan-shaped irradiation region all which an illumination light is shone by illumination apparatuses 112 to 118. A graph (chain double-dashed line) designated by reference character a in FIG. 14 represents a luminance distribution produced by the illumination apparatus 112 (or 116), and a graph (alternate long and short dash line) designated by reference character b in FIG. 14 represents a luminance distribution produced by the illumination apparatus 114 (or 118). The luminance distribution of an irradiation region (inside of fan-shaped pattern) irradiated by the pair of illumination apparatuses 112 and 114 (or pair of 116 and 118) on the left and right is obtained by superimposition of the graphs designated by reference characters a and b, as designated by reference character c, and an approximately constant luminance distribution is obtained over the entire range of the field of view.

In this connection, for inspection of an edge portion, in addition to the texture, illumination of a plurality of circumferential directions is also effective. A chamfered portion is included in the outer circumferential edge, and it is important to inspect for the adherence of dust at the chamfered portion.

Figure 15:
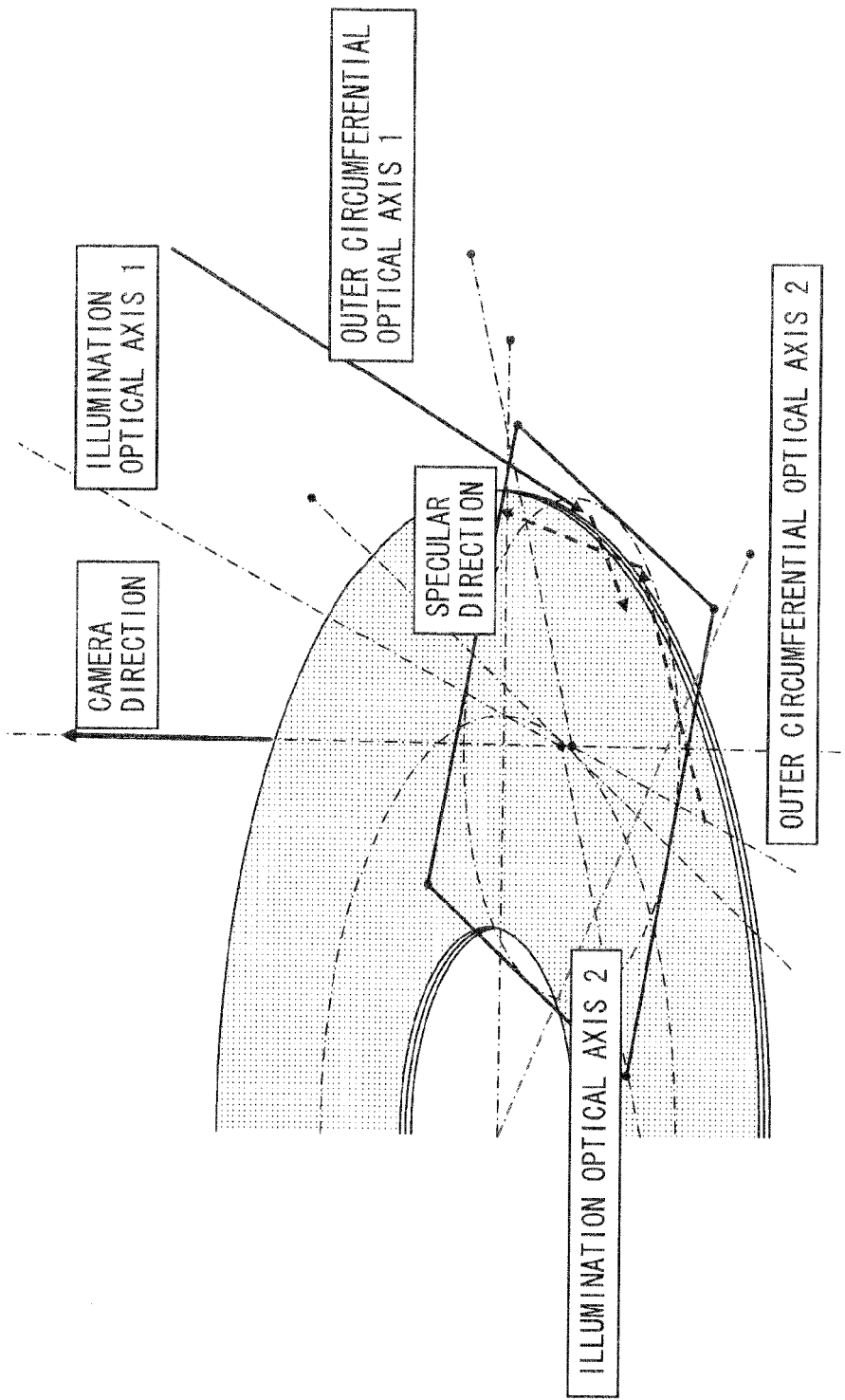
FIG. 15 is an explanatory view used to explain a method of illuminating an edge part of a disk.

Illumination directions that can illuminate the disk end face and the chamfered portion and from which there is no direct reflection from the chamfered portion in the camera direction are, as shown in FIG. 15, directions along the circumferential direction of the disk 12 ("outer circumferential optical axis 1" and "outer circumferential optical axis 2"). Further, since the edge on the distant side is shadowed when the disk is illuminated in the circumferential direction, illumination from a plurality of directions ("outer circumferential optical axis 1" direction and "outer circumferential optical axis 2" direction) is required.

A region that cameras 102 and 104 can image with one imaging operation is the fan-shaped portion that covers a 45 degree range as shown in FIG. 13A. After imaging of the relevant region is finished, the disk 12 is rotated 45 degrees and imaging for the next inspection region is performed. Thereafter, imaging is performed by sequentially changing the inspection region while rotating the disk 12 by 45 degrees each time in a similar manner, to thereby perform imaging for the entire region of the disk 12.

<Description of Inspection Equipment (System)>

Figure 16:
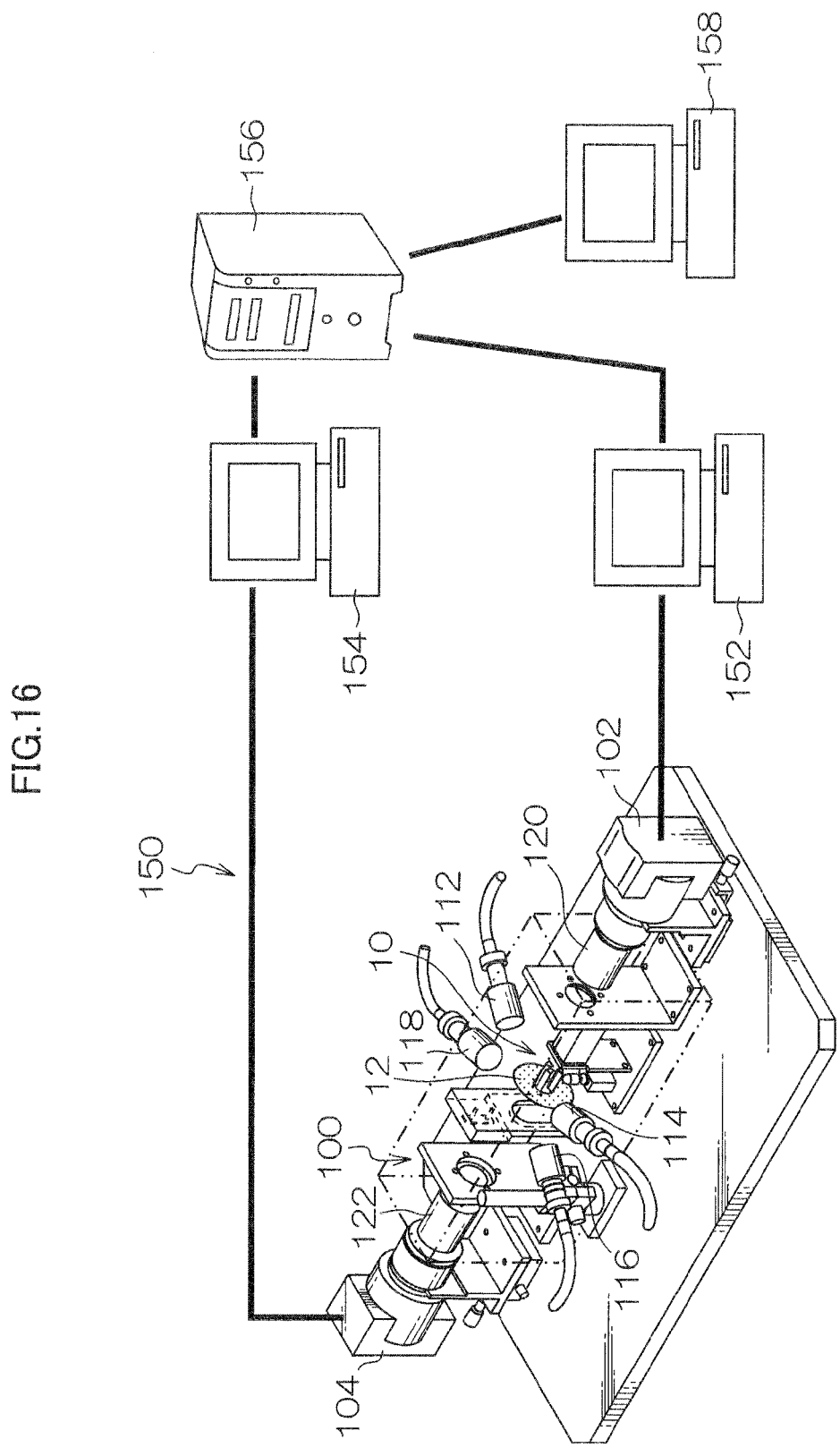
FIG. 16 is a configuration diagram of an inspection system including a disk inspection apparatus.

FIG. 16 is a view that shows a configuration example of an inspection system including the disk inspection apparatus. A system 150 shown in FIG. 16 includes a computer (image processing and system control computer) 152 that performs processing of image data obtained from the camera 102 and control of the overall system, a computer (image processing computer) 154 that performs processing of image data obtained from the camera 104, a data server 156, and a computer (analytical processing computer) 158 that performs analytical processing of an inspection image. In this connection, known communication interfaces can be used for connection devices between the computers (152, 154) and the corresponding cameras (102, 104) as well as connection devices between the data server 156 and each computer (152, 154, 158), irrespective of whether the communication interfaces are wired or wireless.

The image processing and system control computer 152 performs control (lighting/extinction of lighting, control of illumination intensity at the time of lighting, and the like) of the illumination apparatuses 112 to 118, and also controls the cameras 102 and 104 (control of imaging timing, exposure time, and the like) and the motor 24 of the chucking apparatus 10 (switching of inspection regions by rotation of the disk 12 and the like). The image processing and system control computer 152 also performs primary processing (pre-processing) of image data obtained from the camera 102. The primary processing includes differential processing for obtaining information regarding a difference between an inspection image and a dark image and non-linear gradation conversion processing for enhancing dust.

Information for an inspection image that is obtained by the camera 102 is subjected to primary processing by the image processing and system control computer 152, sent to the data server 156 from the image processing and system control computer 152, and stored on the data server 156. Similarly, information for an inspection image that is obtained by the camera 104 is subjected to primary processing by the image processing computer 154, and thereafter stored on the data server 156.

The analytical processing computer 158 performs processing that analyzes data that is stored inside the data server 156. As an example of the analytical processing, the analytical processing computer 158 performs extraction of an image of a region inside the recording surface; extraction of an image of an outer circumferential edge part; extraction of an image of an inner circumferential edge part; detection of the position, number, and dust size of pieces of dust that adhere to each region with respect to the recording surface inner region and the inner and outer circumferential edge regions; and analysis of the inspection result (pass/fail judgment or the like) regarding dust adherence for the entire disk. Furthermore, as a measurement analysis function, the analytical processing computer 158 includes a mapping function for presenting information that facilitates visual ascertainment of the positions and sizes of dust on a disk.

By the above described inspections for a single field of view (45 degree range) being joined together to cover a 360 degree range (eight inspections), it is possible to ascertain the locations on the disk at which dust is adhered as well as the approximate size of the dust. The analytical processing computer 158 organizes information regarding the location of dust, the size of the dust, the overall number of pieces of dust and the like, and compares that information with predetermined pass/fail judgment criteria to perform a pass/fail judgment. The relevant measurement result information is stored in the data server 156.

In this connection, the functions of the analytical processing computer 158 may also be provided in another computer (152 or 154).

<Software Configuration>

Figure 17:
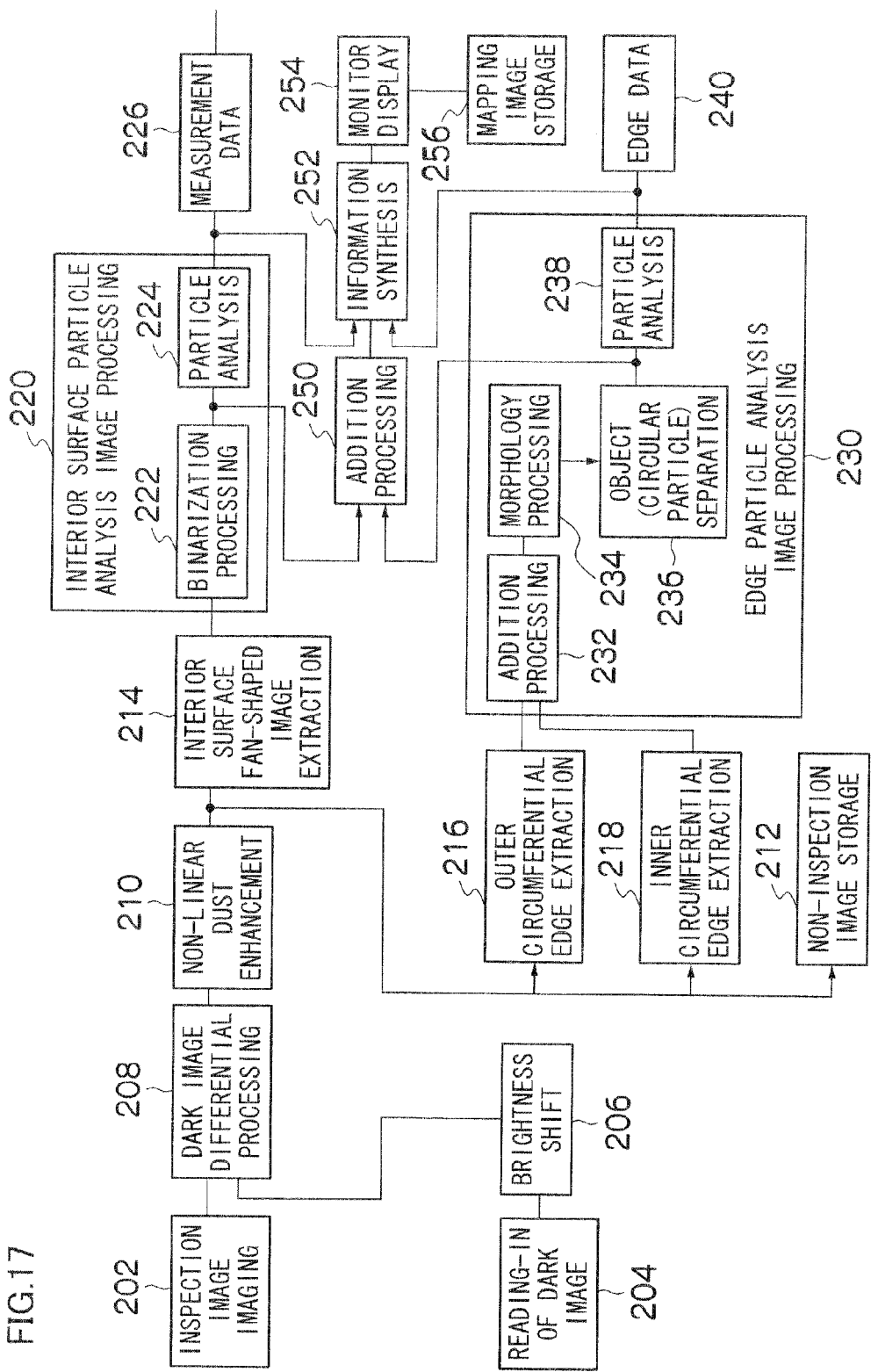
FIG. 17 is a processing block diagram that illustrates the flow of processing in the inspection system of the present example.

FIG. 17 is a processing block diagram that illustrates the flow of processing in the inspection system of the present example. In this connection, the processing function of each block is implemented by software (programs).

First, imaging (one shot; amount of one field of view) of the disk that is an inspection object is performed by the camera 102 (or 104), and digital image data of an inspection image that includes a fan-shaped illumination light irradiation region (⅛ disk region) of the disk that is the inspection object disk is captured (#202).

Meanwhile, data of a dark image acquired by executing an imaging operation when the lens of the camera 102 (or 104) has been previously covered is captured (#204), and a brightness shift computation (subtraction) is performed using a predetermined constant with respect to the relevant dark image (#206).

Next, at a dark image differential processing part (#208), the original inspection image of #202 and the dark image data of #204 are input, and processing (differential processing) is performed that subtracts the dark image (dark noise components) from the original inspection image. Further, conversion processing using non-linear input-output characteristics (for example, log processing) is performed on the image data after the differential processing, at a non-linear dust enhancement processing part (#210) for enhancing portions of dust. The data obtained following the processing by the non-linear dust enhancement processing part (#210) is stored as an image to be inspected (original image) (#212).

Further, based on the original image, the respective processing for interior surface fan-shaped image extraction (#214), outer circumferential edge extraction (#216), and inner circumferential edge extraction (#218) are executed.

The processing ((#214 to #216) which extracts these regions is performed as follows.

Figure 18:
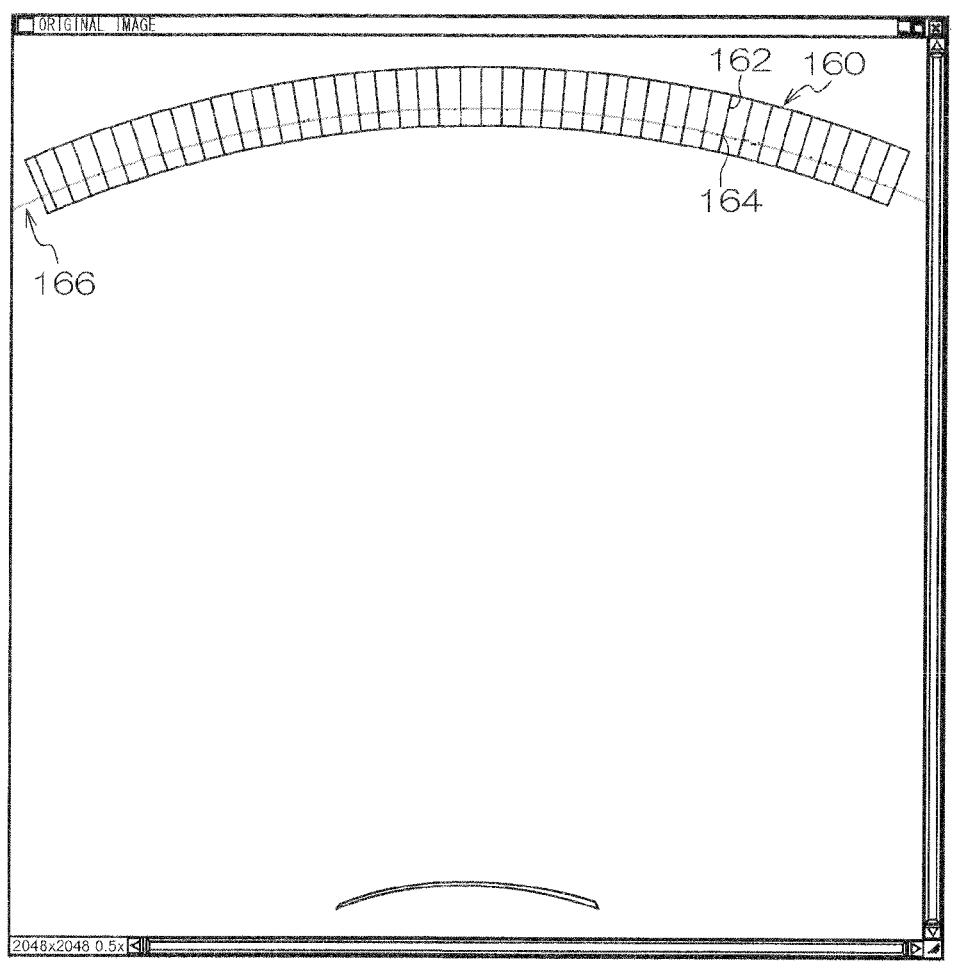
FIG. 18 is an explanatory view of an operation that determines an outer circumferential circular line based on an inspection image.

First, as shown in FIG. 18, a processing window 160 is set for a region in the vicinity of the outer circumferential edge of the disk in the original image, a plurality of scanning positions are decided at regular intervals along the circumferential direction with regard to the processing window 160, and scanning is performed on a straight line 162 along the diametrical direction at each scan position to detect an edge point 164 of the object.

Figure 19:
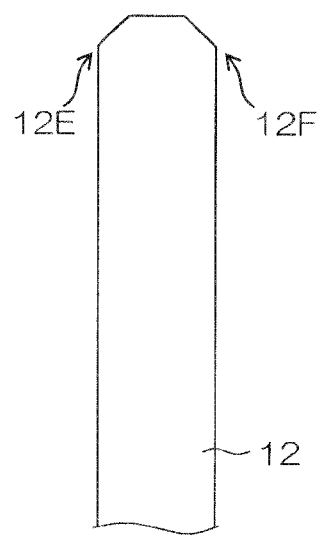
FIG. 19 is an enlarged lateral view of an outer circumferential portion of a disk.

When edge points 164 have been detected for all scan positions, an outer circumferential circular line 166 is determined by a calculation that is based on the detected edge points 164. In this connection, as shown in FIG. 19, the outer circumferential circular line 166 calculated at this time is a line that determines by calculation the position of an inside or outside edge (designated by reference numeral 12E or 12F) of a chamfered outer circumferential end face of the disk 12.

Figure 20:
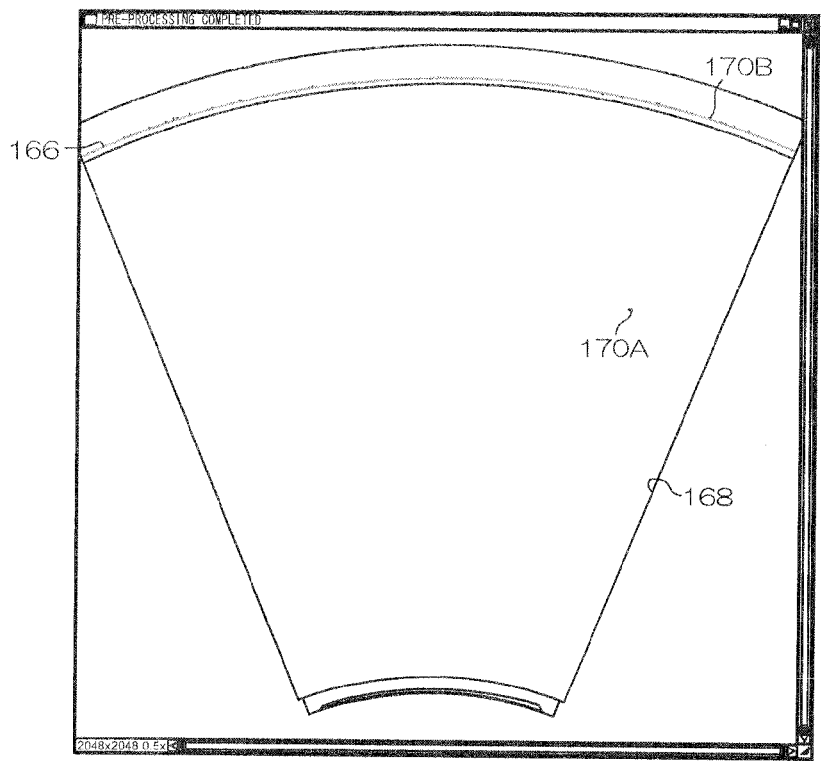
FIG. 20 is a view that illustrates an example of a window image that has undergone an enhancement process.

Further, a center position (coordinates) from the determined outer circumferential circular line 166 and a radius are determined by calculation, and a window (fan-shaped inspection window of a 45 degree range with respect to the center) 168 of an inspection region corresponding to the disk shape is depicted (see FIG. 20).

Figure 21:
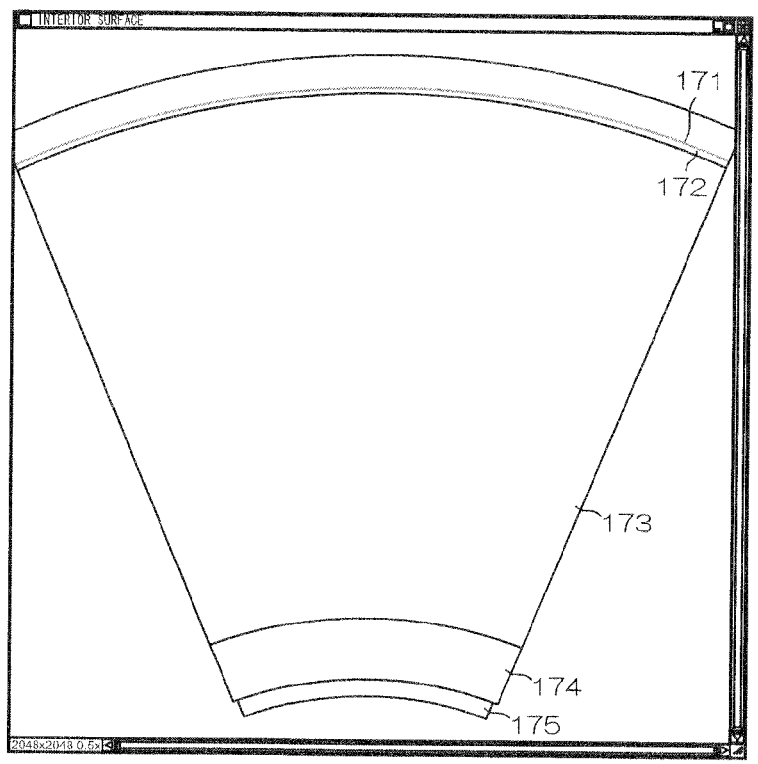
FIG. 21 is a view showing an example of processing window segments for separate regions in an inspection image.

FIG. 21 shows an example of an image in which the lines of the inspection window 168 are added to an inspection image that has undergone the pre-processing as described above. By performing enhancement processing or differential processing or the like with respect to image pixels within the inspection window 168, reflections (objects within the image as designated by reference numerals 170A and 170B) caused by dust on the disk surface can be easily ascertained.

Based on the design value of the disk 12 that is the object for inspection, as shown in FIG. 21, the fan-shaped window image can be divided into five regions (processing windows) comprising an outer circumferential edge region 171, an outside non-recording surface region 172, a recording surface region 173, an inside non-recording surface region 174, and an inner circumferential edge region 175. The number of pieces of dust and the like can be measured for each of these regions.

The "outside non-recording surface region 172", the "recording surface region 173", and the "inside non-recording surface region 174" correspond to an interior surface fan-shaped image, and interior surface particle analysis image processing is performed with respect to the interior surface fan-shaped image (#220 in FIG. 17). The interior surface particle analysis image processing (#220) includes binarization processing (#222) and particle analysis processing (#224).

The binarization processing (#222) is processing that compares the digital value (gradation value) of an image signal with a predetermined threshold value and extracts portions with a higher brightness than the threshold value. When there is dust on the interior surface of a disk, the illumination light is scattered by the dust, and hence the piece of dust is reflected in the image as a bright spot that is in accordance with the size of the piece of dust. The dust can then be detected by performing a comparison with a threshold value that is previously set in conformity with the level of dust to be detected. By means of this binarization processing, pixels (processing objects) corresponding to the dust are separated. An object that is a region or a group in which pixels of the same brightness level obtained by the binarization processing (#222) are combined is defined as a "particle".

The particle analysis processing (#224) includes an analytic function that generates information relating to particles of an image, and acquires information such as the position, shape, size, number and the like of particles. Data for a measurement value of each item obtained by the particle analysis processing (#224) is stored in a file as measurement data (#226).

Meanwhile, the "outer circumferential edge region" and the "inner circumferential edge region" are subjected to edge particle analysis image processing (#230) that deals with issues that are specific to an edge region. More specifically, because an edge part of a disk includes factors other than dust, such as reflection from a chamfered portion, deposition defects, and flaws, processing is performed to separate dust (particles) and factors other than dust for an edge region in order to detect only dust. The inside edge processing is performed only on portions at which the claws (16, 17, 18) do not exist by switching according to the existence/non-existence of the claws (16, 17, 18).

The edge particle analysis image processing (#230) includes addition processing (#232), morphology processing (#234), circular particle separation processing (#236), and particle analysis processing (#238).

The addition processing (#232) is processing that combines information for the outer circumferential edge region with information for the inner circumferential edge region.

The morphology processing (#234) is processing that changes the shape of a figure by an inter-image operation, and in this case performs processing in the order of reduction→enlargement. While image portions resulting from a reflection of a chamfered portion or a flaw such as a deposition defect are long and narrow belt-shaped lines along an edge line, an image portion resulting from dust (particles) reflects the individual piece of dust and is approximately circular, or in a case in which a plurality of pieces of dust are adhered in an adjoining manner, the relevant image portion forms a shape ("string-of-beads"-like shape) in which circular shapes corresponding to each piece of dust partially overlap in a consecutive manner. Hence, by means of the morphology processing (reduction→enlargement), image portions resulting from flaws such as reflection of chamfered portions or deposition defects are removed as noise components, and image portions caused by dust (particles) are highlighted and remain. In this connection, processing that judges an "aspect ratio" or the like may be used in place of the morphology processing, or in combination therewith.

The circular particle separation processing (#236) serves as a filter that separates circular particles from the data after morphology processing (#234), and includes processing that separates an object at recessed portions of a "string-of-beads"-like image part in which the thickness changes, and circle detection processing that detects circular particles based on the circularity of the individually separated objects.

The particle analysis processing (#238) includes an analytic function that generates information relating to circular particles that have undergone an object separation process, and acquires information such as the position, shape, size and number of particles. Data for measurement values of each item obtained by the particle analysis processing (#238) is stored in a file as edge data (#240).

An image of a particle obtained by the binarization processing (#222) of the interior surface particle analysis image processing (#220) and an image of a particle obtained by the object separation processing (#236) of the edge particle analysis image processing (#230) are superimposed by the addition processing (#250), and character information (numerical value labels) of a measurement result obtained by the particle analysis processing (#224, #238) is assigned to each particle on the screen and synthesized (#252), and thereafter displayed on a monitor as an inspection result (#254). An image onto which the measurement result has been mapped is stored in a file as a mapping image (#256).

Figure 22:
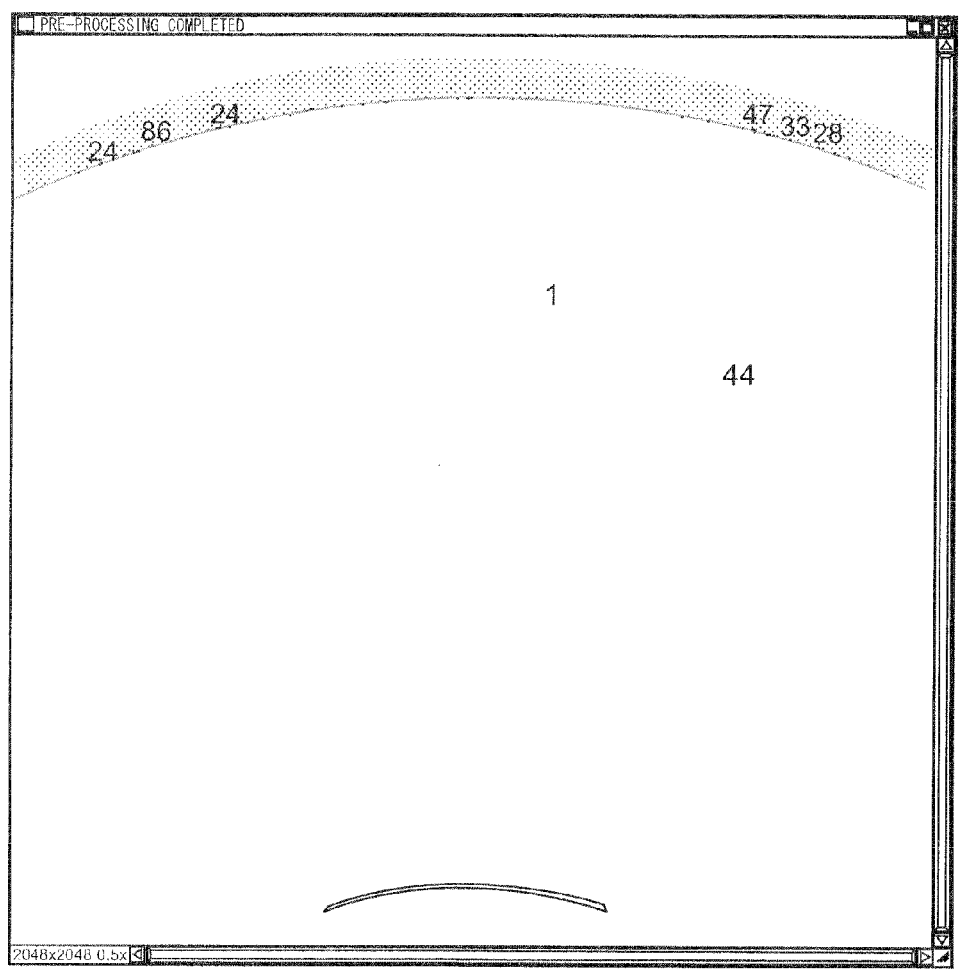
FIG. 22 is a view showing an image example (for one inspection image) of a measurement result.

FIG. 22 shows an image example of an inspection result. A numerical value label that is assigned to a particle (dust) shows the size of the particle. It is preferable to vary the display color depending on whether or not the particle size is a value within an allowable range, or according to the adherence position of the particle and the like. A setting may also be made in which an allowable particle size varies depending on whether a dust adherence position is an edge region or is an interior surface region.

For example, a blue numerical value label indicates a measurement result in an edge region. A green numerical value label indicates a measurement result within an allowable range (when the result is OK) in an interior surface region. A red numerical value label indicates a measurement result at the time of a failure judgment (when the result is NG) that exceeds an allowable range.

Figure 23:
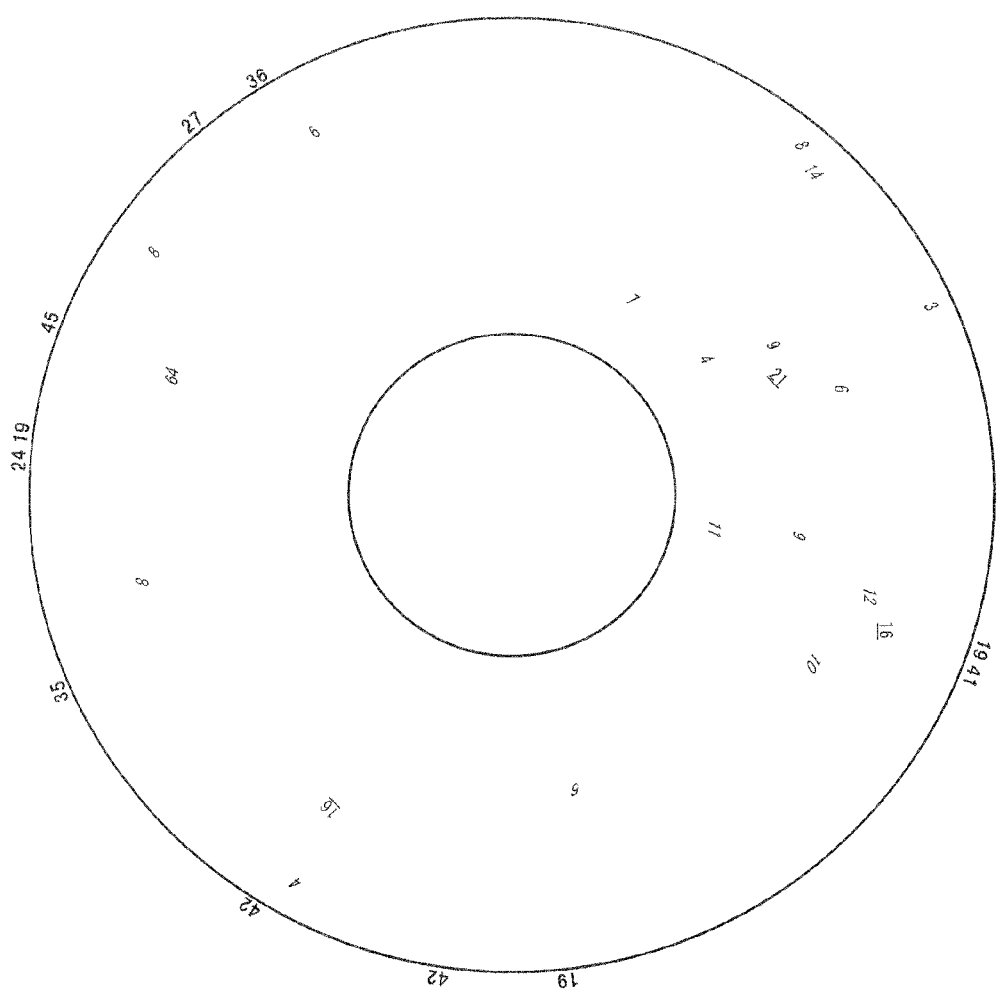
FIG. 23 is a view showing an image example (entire one side of one disk) of a measurement result.

By joining together measurement results for fan-shaped inspection regions of a 45-degree range to cover a total range of 360 degrees (eight regions) in this way, as shown in FIG. 23, a measurement result for the entire disk surface can be displayed. In FIG. 23, the blue, the green and the red numerical value label is shown by a bold face type, italic type and underline number respectively <System Control Example>

Figure 24:
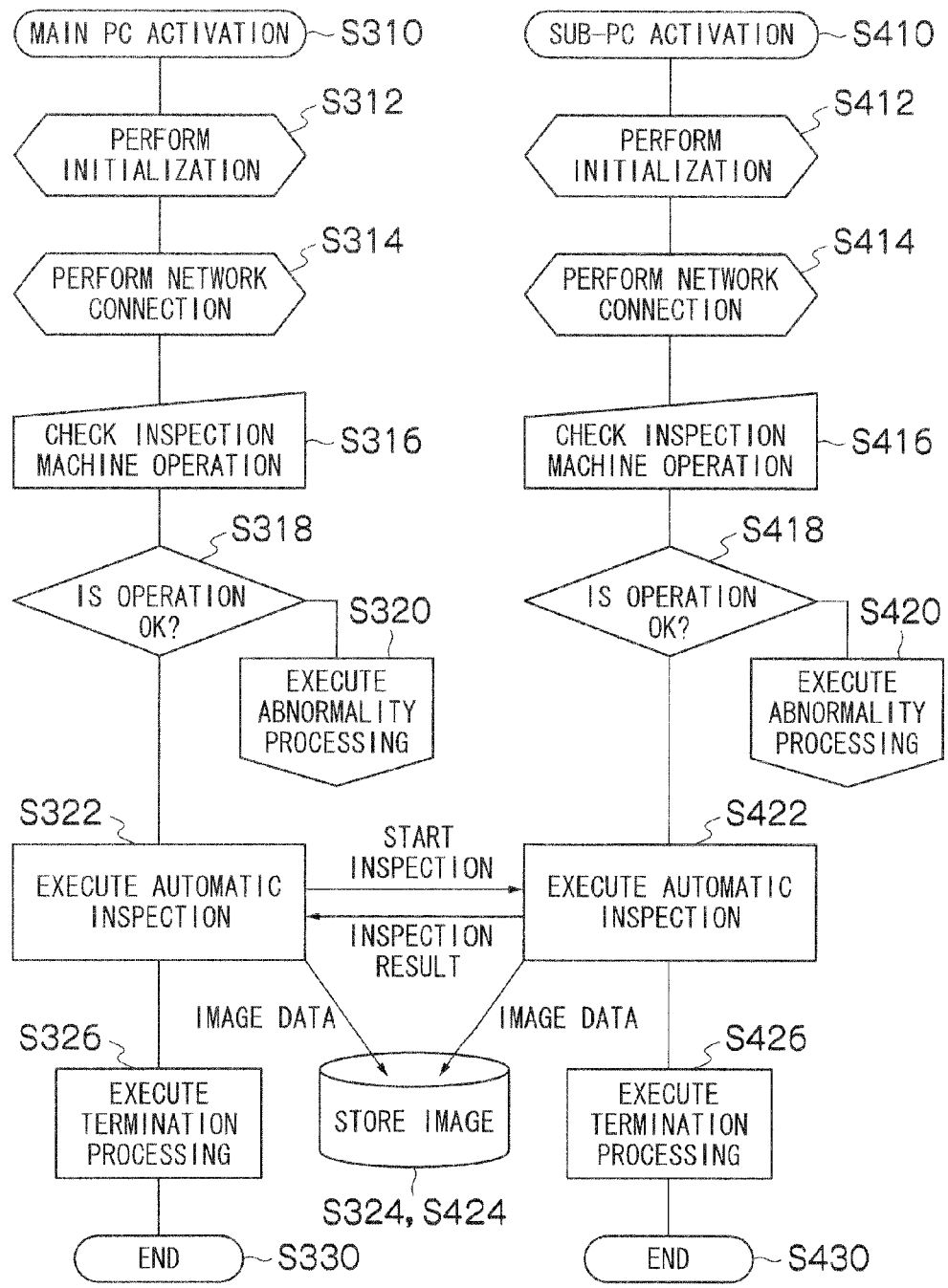
FIG. 24 is a flowchart illustrating a control example of an inspection system.

FIG. 24 is a flowchart that illustrates an example in which the present system is controlled using two computers. The main PC processing that is shown on the left side in FIG. 24 corresponds to the computer designated by reference numeral 152 in FIG. 16, and performs an inspection of a first surface (for example, a front surface) of the disk 12. Further, the sub PC processing that is shown on the right side in FIG. 24 corresponds to the computer designated by reference numeral 154 in FIG. 16, and performs an inspection of a second surface (for example, a rear surface) of the disk 12.

According to the present example, in consideration of the load involved in image transfer and image processing, an example is described in which processing is alternately executed using two computers, one for front surface inspection and one for rear surface inspection. However, it is also possible to realize the processing of these two computers using a single computer that has a high processing speed and processing capacity.

As shown in FIG. 24, after starting up both the main PC and the sub PC (steps S310 and S410) and performing initialization (steps S312 and S412), a network connection is established (steps S314 and S414).

Next, the operation of the inspection machine is checked by cooperative operations between the chucking apparatus 10 and the respective cameras 102 and 104 (steps S316 and S416). This checking of the operation of the inspection machine may be performed automatically for predetermined check items in accordance with a predetermined program or, as necessary, may be performed by an operator performing an operation to input numerical values or the like.

It is determined whether or not the operation of the inspection machine is normal based on the process that checks the operation thereof (steps S318, S418), and if an abnormality is confirmed, predetermined processing (abnormality processing) is performed to deal with the abnormality (steps S320, S420). In contrast, if it is confirmed that the operation of the inspection machine is normal, an automatic inspection process (steps S322, S422) starts.

As described in detail later, according to the present example imaging of a front surface of a disk and imaging of a rear surface of the disk are alternately performed. Initially, imaging of a first surface is performed by the main PC, and after that imaging the main PC sends an instruction to start inspection to the sub PC. Upon receiving the instruction, the sub PC executes imaging of the rear surface. When imaging and inspection (image analysis processing) of the image by the sub PC ends, the inspection result is sent to the main PC. Further, the image data (image data to be inspected and mapping image data) that is processed by the main PC is sent to a server computer and stored in a storage area of the server computer (steps S324, S424).

After acquiring image data for the front surface and the rear surface, respectively, the chucking apparatus is rotatingly driven to rotate the disk 12 by 45 degrees and stops the disk 12 at that position. Thereafter, similarly to the above described case, imaging of the front and rear surfaces of the disk is performed, and the respective inspection images are analyzed. In this manner, while rotating the disk 45 degrees each time, imaging of the front and rear of the disk is performed at each of the following stopping positions: 0 degree position, 45 degree position, 90 degree position, 135 degree position, 180 degree position, 225 degree position, 270 degree position, and 315 degree position. Thus, for a single disk, a total of 16 pieces of image data (fan-shaped images) are acquired by obtaining eight images for each side of the disk.

When all of the inspections are completed, termination processing is performed (steps S326, S426) and the processing ends (steps S330, S430).

Next, an automatic inspection process is described.

Figure 25:
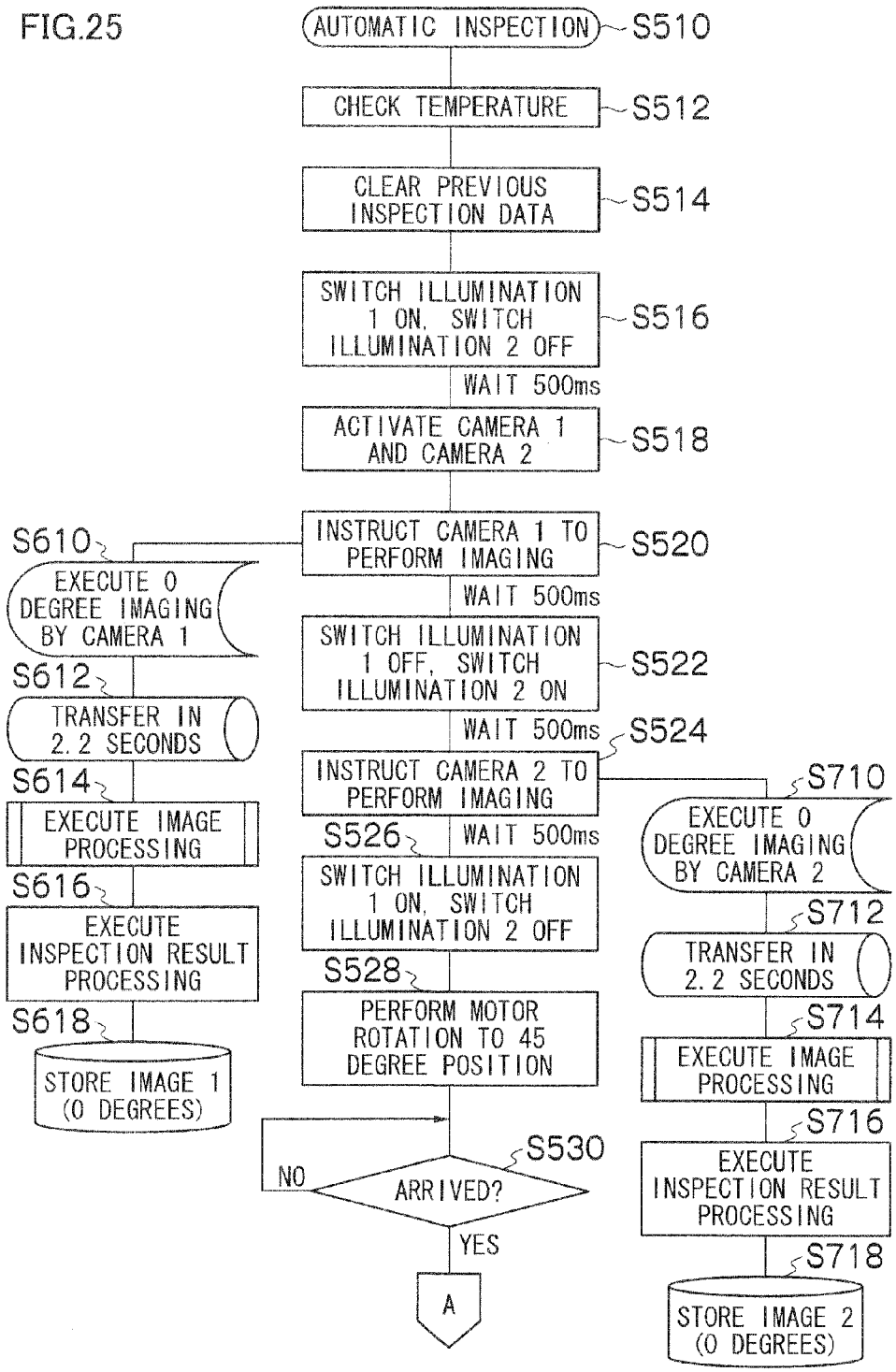
FIG. 25 is a flowchart illustrating procedures of an automatic inspection process.
Figure 26:
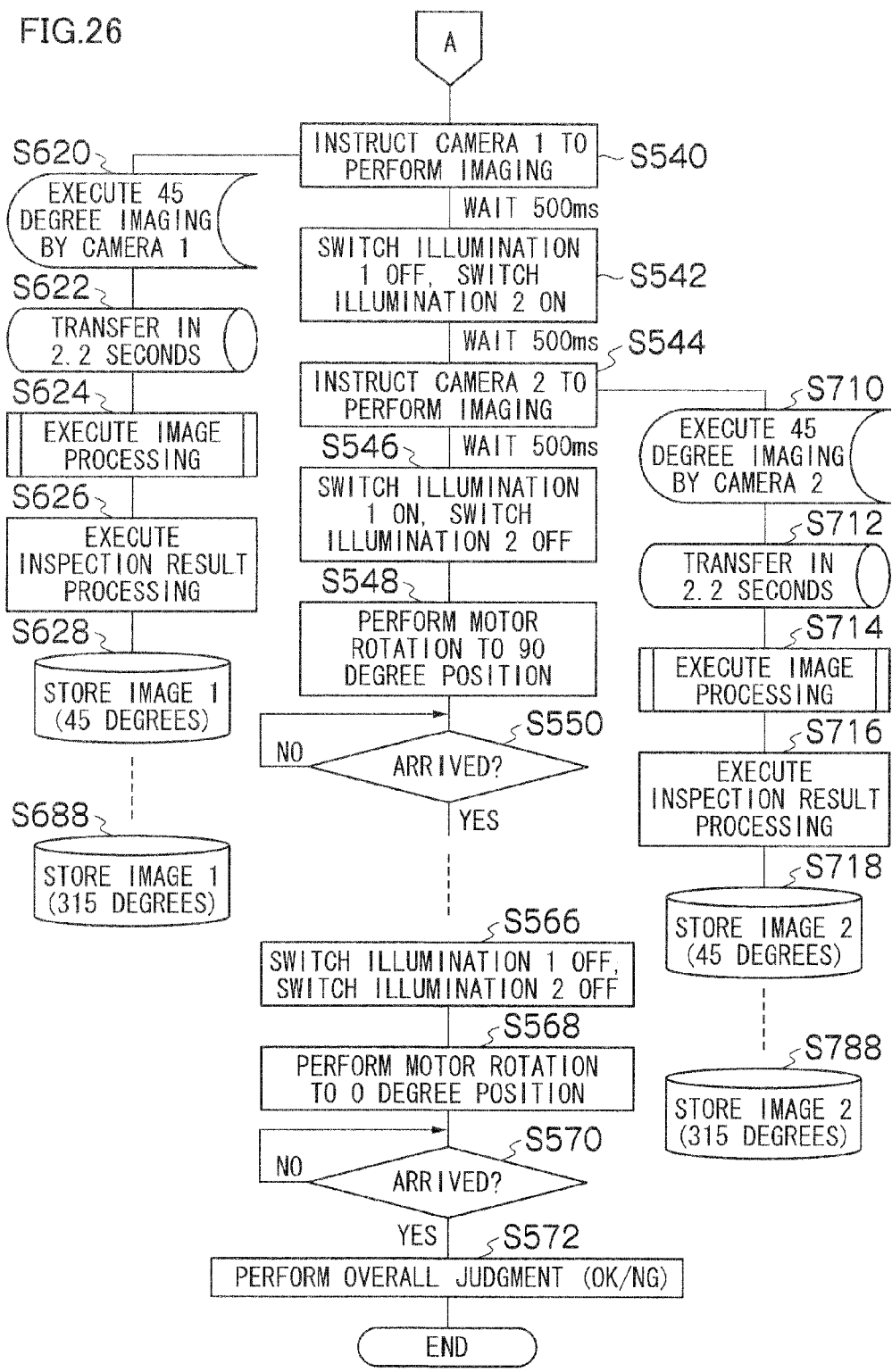
FIG. 26 is a flowchart illustrating procedures of an automatic inspection process.

FIG. 25 and FIG. 26 are flowcharts that illustrate the processing procedures of an automatic inspection. The flow described in the center of each of FIG. 25 and FIG. 26 is a system control flow that is executed by the main PC. The flow described on the left side of FIG. 25 and FIG. 26 is a flow of imaging and image processing performed by a first camera (corresponds to a camera designated by reference numeral 102 in FIG. 10; abbreviated to "camera 1"). The flow described on the right side of FIG. 25 and FIG. 26 is a flow of imaging and image processing performed by a second camera (corresponds to a camera designated by reference numeral 104 in FIG. 10; abbreviated to "camera 2"). According to the present system, the main PC performs control of the system and the processing of camera 1. The sub PC performs the processing of camera 2.

When the automatic inspection process starts (step S510), first a temperature check is performed (step S512), and the inspection data from the previous time is cleared (step S514). Subsequently, the pair of illumination apparatuses on the camera 1 side (abbreviated to "illumination 1") are switched on (ON), and the pair of illumination apparatuses on the camera 2 side (abbreviated to "illumination 2") are switched off (OFF) (step S516). After waiting for a predetermined time (for example, 500 ms), activation of the camera 1 and the camera 2 is performed (step S518), and an instruction to execute imaging is issued to the camera 1 (step S520). At this time, a dedicated folder for camera 1 and camera 2, respectively, is created at the server to prepare for storage of inspection images. The folder names are, for example, automatically generated as "sample name+sequential number+1 cam" and "sample name+sequential number+2 cam".

Based on the imaging instruction in step S520, imaging at the 0 degree position (initial position when disk rotation control of the chucking apparatus is performed) is executed by the camera 1 (step S610). The data of the image that is imaged by the camera 1 is transferred to a computer (in this case, the main PC also serves as the computer) (step S612). According to the present example, a transfer time of 2.2 seconds is secured.

Based on the picked-up image that has been transferred thereto, the computer performs image processing using the software described in FIG. 17 (step S614 in FIG. 25), and performs processing to combine the inspection result into the displayed screen (step S616). A mapped image of the inspection result obtained in this manner and the image to be inspected (original image) are stored in a dedicated folder at the server (step S618).

A filename is automatically generated as "sample name+ sequential number+(X, Θ)". In this case, the "X" in (X, Θ) is a variable that distinguishes between camera 1 and camera 2. X=1 for an image picked up by camera 1, and X=2 for an image captured by camera 2. "Θ" is a variable that specifies an imaging position (rotational position reached by chucking) of a disk, and Θ specifies any one of the eight positions comprising 0 degrees, 45 degrees, 90 degrees . . . 315 degrees. In the drawings, an image that is picked up by camera 1 is described as "image 1", and an image picked up by camera 2 is described as "image 2".

After an instruction to execute imaging is output to the camera 1 in step S520 and imaging by the camera 1 has been executed, the system waits for a predetermined time (for example, 500 ms), and then switches off the illumination 1 and switches on the illumination 2 (step S522). Next, after waiting for a predetermined time (for example, 500 ms), an instruction to execute imaging is issued to the camera 2 (step S524).

Based on the imaging instruction, the camera 2 executes imaging of the 0 degree position (step S710). The data of the image that is imaged by the camera 2 is transferred to a computer (in this case, the sub PC) (step S712). According to the present example, a transfer time of 2.2 seconds is secured.

Based on the picked-up image that has been transferred thereto, the computer performs image processing using the software described in FIG. 17 (step S714 in FIG. 25), and performs processing to combine the inspection result into the displayed screen (step S716). A mapped image of the inspection result obtained in this manner and the image to be inspected (original image) are stored in a dedicated folder at the server (step S718).

After an instruction to execute imaging is output to the camera 2 in step S524 and imaging by the camera 2 has been executed, the system waits for a predetermined time (for example, 500 ms), and then switches on the illumination 1 and switches off the illumination 2 (step S526). Further, the motor of the chucking apparatus is driven to perform rotation to the 45 degree position (step S528). Arrival of the disk at the 45 degree position is monitored during rotation by the motor (step S530), and the motor is stopped upon confirming that the disk has arrived at a predetermined position.

Thereafter, the operation proceeds to step S540 in FIG. 26, and an instruction to execute imaging is issued to the camera 1 (step S540).

Based on the imaging instruction at step S540, the camera 1 executes imaging of the 45 degree position (step S620). Thereafter, predetermined processing (steps S622 to S628) is performed, and a mapped image of the inspection result for the relevant 45 degree position and the image to be inspected (original image) are stored in a dedicated folder at the server (step S628). The processing in steps S622 to S628 is the same as that in steps S612 to S618 described in FIG. 25, and hence a description thereof is omitted.

After an instruction to execute imaging is output to the camera 1 in step S540 in FIG. 26 and imaging by the camera 1 has been executed, the system waits for a predetermined time (for example, 500 ms), and then switches off the illumination 1 and switches on the illumination 2 (step S542). Next, after waiting for a predetermined time (for example, 500 ms), an instruction to execute imaging is issued to the camera 2 (step S544).

Based on the imaging instruction, the camera 2 executes imaging of the 45 degree position (step S720). Thereafter, predetermined processing (steps S722 to S728) is performed, and a mapped image of the inspection result for the relevant 45 degree position and the image to be inspected (original image) are stored in a dedicated folder at the server (step S728). The processing in steps S722 to S728 is the same as that in steps S712 to S718 described in FIG. 25, and hence a description thereof is omitted.

After an instruction to execute imaging is output to the camera 2 in step S544 in FIG. 26 and imaging by the camera 2 has been executed, the system waits for a predetermined time (for example, 500 ms), and then switches on the illumination 1 and switches off the illumination 2 (step S546). Further, the motor of the chucking apparatus is driven to perform rotation to the 90 degree position (step S548). Arrival of the disk at the 90 degree position is monitored during rotation by the motor (step S550), and the motor is stopped upon confirming that the disk has arrived at the predetermined position.

Although a description of the operations thereafter is omitted herein, similarly to the operations described above, imaging by the camera 1 and imaging by the camera 2 are alternately performed to obtain images at the 135 degree position, 180 degree position, 225 degree position, 270 degree position, and 315 degree position, respectively, and an inspection is performed by analyzing each image. Thus, the same processing is repeated, and when imaging at the 315 degree position and storage of the captured image (steps S688 and S788) are completed, the illumination 1 and the illumination 2 are both switched off (step S566).

Thereafter, the motor of the chucking apparatus is driven to perform rotation to the 0 degree position (step S568). Arrival of the disk at the 0 degree position is monitored during rotation by the motor (step S570), and the motor is stopped upon confirming that the disk has arrived at the predetermined position.

In this manner, overall judgment is performed of a total of 16 inspection images comprising eight images for the front and rear, respectively, to thereby determine whether the relevant disk passed or failed (OK/NG) the inspection (step S572). The pass/fail criteria can be appropriately set and changed from an input device such as a keyboard by the operator. Based on the relevant pass/fail criteria that have been set, an inspection result is automatically determined in accordance with the program, and the result that is determined is notified (displayed on a display or the like) to the operator. Further, it is also possible to utilize the determined result to control a screening apparatus so as to automatically distinguish between disks that failed inspection and disks that passed inspection.

<Disk Inspection Flow>

Figure 27:
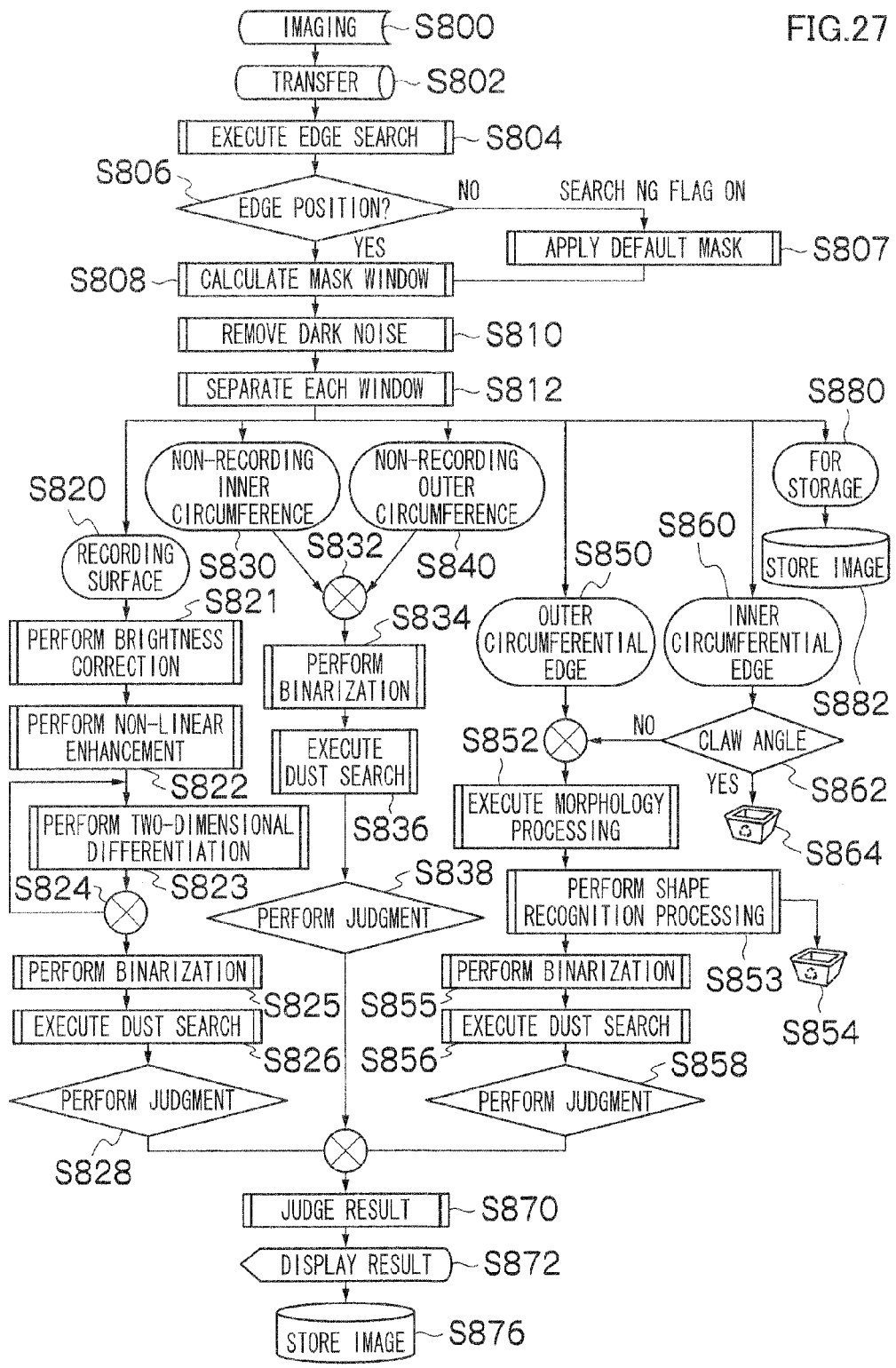
FIG. 27 is a flowchart illustrating processing procedures of a disk inspection according to the present embodiment.

FIG. 27 is a flowchart that illustrates the procedures of a disk inspection according to the present embodiment.

A disk that is an object for inspection is imaged with a CCD camera (step S800), and data of the captured image is transferred to a computer (PC) from the CCD camera (step S802).

Based on the captured image, the computer first performs edge search processing (step S804). The edge search processing is arithmetic processing that detects an edge position (outer circumferential edge position) of the disk. If an edge position is found by the edge search processing ("YES" at step S806), a mask window is calculated based thereon and a window (inspection window) is set (step S808).

In contrast, when an edge position is not detected with the edge search processing and the edge position judgment in step 806 is "NO", a search NG flag is set to "ON" and a default mask is applied (step S807).

Subsequently, processing is performed that removes dark noise held by each pixel (light-receiving cell) of the CCD from the captured raw image (step S810). A dark noise component is removed by previously capturing a completely black image and acquiring dark noise data, and then taking differences with the relevant dark noise data from the inspection image (raw image).

Based on an image obtained in this manner, processing is performed to separate the window into five windows that correspond to "recording surface (recording region in which servo signal or the like is written)", "non-recording inner circumferential region", "non-recording outer circumferential region", "outer circumferential edge region", and "inner circumferential edge region", respectively (step S812). These regions correspond to "recording surface region 173", "inside non-recording surface region 174", "outside non-recording surface region 172", "outer circumferential edge region 171", and "inner circumferential edge region 175" described in FIG. 21, respectively.

The window separation processing utilizes information concerning the specifications of the hard disk that is the inspection object. It is assumed that the specifications for the hard disk indicate an inner diameter R1, an outer diameter R2, and a recording region that is a range of radius Ra to radius Rb from the disk center (R1<Ra<Rb<R2). Further, it is assumed that a non-recording inner circumferential region is a range of radius Rc to radius Ra from the disk center, and a non-recording outer circumferential region is a range of radius Rb to radius Rd from the disk center (R1<Rc<Ra<Rb<Rd<R2).

Regarding a method which acquires such specification information, a method can be adopted in which an operator manually inputs the information from an input device such as a keyboard or a mouse of a computer, or in which a plurality of kinds of specification information that correspond to a plurality of kinds of disks are stored in advance inside a storage device of a computer and the corresponding specification (disk type) is selected at the time of an inspection, or in which the specification information is read from a storage medium such as a memory card.

The system refers to the relevant specification information and, with respect to the captured image, sets the range of radius Ra to radius Rb from the disk center as a "recording surface window", sets the range of radius Rc to radius Ra as a "non-recording inner circumferential window", sets the range of radius Rb to radius Rd as a "non-recording outer circumferential window", sets the range of radius Rd to radius Re as an "outer circumferential edge window", and sets the range of radius Rf to radius Rc as an "inner circumferential edge window". Provided that, Re is a predetermined value that satisfies R2<Re, and Rf is a predetermined value that satisfies Rf<R1.

For example, in the case of a disk (R1=10 mm, R2=32.5 mm) with an outer diameter of 2.5 inches, Ra=15 mm, Rb=30 mm, Re=33.0 mm, and Rf=9.5 mm.

Thus, the window is separated into five windows, and the processing operation branches for each window. Hereunder, a recording surface window processing routine (step S820), a non-recording inner circumferential window processing routine (step S830) a non-recording outer circumferential window processing routine (step S840), an outer circumferential edge window processing routine (step S850), an inner circumferential edge window processing routine (step S860), and a processing routine for storage (S880) are described.

<Recording Surface Window>

An image of a recording surface portion is, as necessary, subjected to brightness correction (step S821), and thereafter non-linear enhancement processing (step S822) and two-dimensional differential processing (step S823) are performed. The brightness correction processing (step S821) can be omitted. In the two-dimensional differential processing (step S823), components produced by a texture or imprinting can be separated by removing a moderate brightness difference by setting a threshold value.

Data obtained by the two-dimensional differential processing in this manner (step S823) is added (step S824) to data obtained with non-linear enhancement processing (step S822) performed before the differential processing, and binarization processing is performed (step S825).

Thereafter, a dust search is performed with respect to the binarization image (step S826). The dust search processing (step S826) referred to here corresponds to processing for particle analysis (#224) described in FIG. 17.

Thus, information regarding the position, shape, size, and number of particles is acquired, and a judgment is performed regarding whether or not the particles are within an allowable range (OK) or are at a failure (NG) level that exceeds an allowable range (step S828 in FIG. 27).

<Non-Recording Inner Circumferential Window and Non-Recording Outer Circumferential Window>

With respect to images of portions corresponding to a non-recording inner circumferential region and a non-recording outer circumferential region, a dust search (step S836) is performed after performing binarization processing (step S834) for each image. Based on the acquired information, a judgment is performed regarding whether or not particles are within an allowable range (OK) or are at a failure (NG) level that exceeds the allowable range (step S838). The specific processing contents are the same as in step S826 to S828. In this connection, a step designated by reference numeral S832 in FIG. 27 represents switching an input signal.

<Outer Circumferential Edge Window>

As described at #234 in FIG. 17, the outer circumferential edge part is subjected to morphology processing (step S852 in FIG. 27), and thereafter is subjected to shape recognition processing (step S853). The shape recognition processing (step S853) corresponds to object separation (circular particle separation) processing (#236) described in FIG. 14. For example, the ellipticity (aspect ratio) is calculated, objects that have a shape that is close to a round shape are judged to be dust particles, and objects that have a long and narrow shape are judged to be flaws or deposition defects.

After separating pixels into objects that could be separated (dust) and objects that could not be separated (objects in which a plurality of pixels linked, i.e. flaws or deposition defects or the like) by morphology processing, only the dust information is retained, and the flaw (defect) information is deleted (step S854).

Binarization is performed on an image that includes dust information (step S855), and a dust search (step S856) and judgment are performed on the binarization image (step S858). The dust search processing (step S856) corresponds to particle analysis (#224) processing described in FIG. 17, and the judgment processing (step S858) is the same as in steps S828 and S838.

<Inner Circumferential Edge Window>

With respect to the inner circumferential edge part, it is judged whether or not the image is an image of the same angle positions as the claws 16, 17, and 18 in the chucking apparatus 10 (step S862). Processing that is the same as that for the outer circumferential edge part (steps S852 to S858) is performed only when the image does not match the claw angles (time of NO judgment in step S862). When the image matches the claw angles (time of YES judgment in step S862), dust analytical processing for the inner circumferential edge is skipped (step S864).

The dust search and the judgment result thereof for each processing window performed as described above are integrated (step S870), and an inspection result with respect to that result can be displayed on a monitor (step S872).

For the result display, an overlay display with respect to the inspection image is performed with an image processing engine. More specifically, negative/positive inversion processing is performed for a captured image, dust positions are plotted thereon, and labels are attached that specify the size of dust particles. Since a captured image from a CCD camera is an image in which bright spots of dust shine whitely on a black background, on a monitor display of the inspection result the captured image is subjected to negative/positive inversion to obtain an image containing black dust spots on a white background. On this inverted image, positions of dust that are detected by the dust searches (steps S826, S836, and S856) are plotted, and numerical values that show the size of each dust particle are also added thereto. If a dust size is within an allowable range that is previously determined for each region, a green or blue label to added, and if the dust size exceeds an allowable range a red label is added thereto (see FIG. 22).

Thus, a mapping image to which is added an overlay display of dust information is output to the monitor of a computer display or another display device and stored as an image file (step S876), and the positions and sizes of dust particles are stored in a separate file as text data.

Further, when the respective window separation processing operations are performed at step S812, the original image is also stored in an image file as a storage image (step S882).

There are the following advantages according to the disk inspection apparatus 100 of the present embodiment.

(1) A minimum detection capability of 0.1 µm can be achieved.

(2) A two-sided simultaneous inspection can be performed without turning over (inverting or the like) the disk.

(3) Inspection for dust adherence can be performed not only within a recording surface, but also at an outer circumferential edge region and an inner circumferential edge region.

(4) Imprinting to a recording surface and abnormal reflection of light by a disk edge or a claw of the chucking apparatus 10 is suppressed.

(5) The influence of a difference in sensitivity between a flat part and an edge part of a hard disk can be avoided. A sensitivity when detecting dust adhered on a hard disk from a picked-up image is around 100 times higher for a flat part compared to an edge, and it is only possible to inspect one of a flat part and a edge part using a common threshold value level setting. However, according to the present embodiment, since an inspection image is divided into five regions and appropriate image processing is executed for each region, a flat part and an edge part can be simultaneously inspected.

(6) It is possible to inspect a region of ⅛ of a disk (corresponds to area of approximately 30 mm per side in the case of a 2.5 inch disk) with one imaging operation using a low-cost CCD camera that captures images of around 4 million pixels. Normally, when a detection object is dust on an interior surface and a sub-µm defect is allocated to one pixel, it is only possible to detect a 4 mm square area based on the resolution of the CCD. In contrast, according to the present embodiment, since a configuration is adopted that causes defects to emerge by subjecting a picked-up image to enhancement processing by performing non-linear enhancement and two-dimensional differentiation, and thereafter superimposing the image on a raw image that has a high brightness and performing binarization, minute dust can be detected at a level that is greater than the resolution of the image pickup element.

(7) By performing two-dimensional differential processing for a recording surface and setting an appropriate threshold value so as to eliminate values smaller than the prescribed threshold value or the like, a moderate brightness difference can be removed. As a result, it is possible to avoid a phenomenon in which an unnecessary reflection produced by the texture on the front surface of a disk, or imprinting a disk, or imprinting of a background of a lens or the like due to the front surface of a disk being a mirror surface becomes noise in a dust detection process.

(8) By applying an algorithm that combines morphology processing and shape recognition processing for an edge part, defects other than dust, such as a flaw or a deposition omission, on the edge can be isolated from adhered dust.

(9) By processing 16-bit image data, common 8-bit minute dust information can be extracted.

(10) Since a configuration is adopted in which an inspection image (raw image) is subjected to inversion processing, dust positions are plotted thereon, labels are attached according to the size of particles, and the inspection result is displayed on a monitor, the positions and sizes of dust particles can be visually distinguished on a monitor during an inspection.

<Further Characteristics of Illumination Optical System>
(*Additional Section Related to Present Specification)

Figure 28:
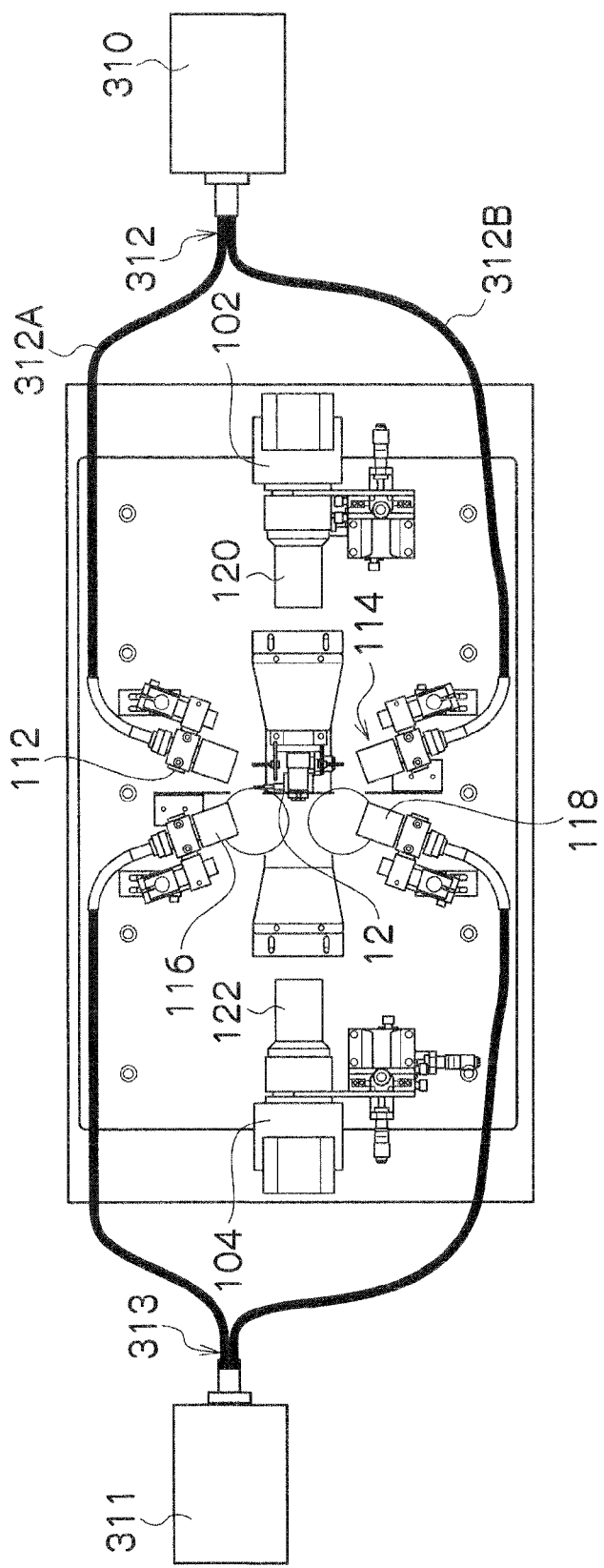
FIG. 28 is a plane view that illustrates a configuration example of an illumination optical system.

FIG. 28 is a plane view that shows a configuration example of an illumination optical system. As shown in FIG. 28, according to the present example, light source apparatuses 310 and 311 are provided for the inspection surface of the front surface side and the rear surface side of the disk 12, respectively. The configuration is such that an optic fiber 312 (or 313) branches in two from a single light source apparatus 310 (or 311) with respect to one side of the disk 12 so that a disk inspection region is symmetrically illuminated from two directions (left and right). Because the same apparatus configuration is adopted for both the front surface side and rear surface side of the disk 12, only one of the illumination optical systems (right side in FIG. 28) will be described here.

As described with FIG. 13A, the illumination apparatuses 112 and 114 according to the present embodiment perform pattern illumination by emitting an illumination light that forms a shape that is approximately the same as an inspection region (inspection range 130) of the disk 12 on only the inspection region and a circumferential part thereof.

Figure 29:
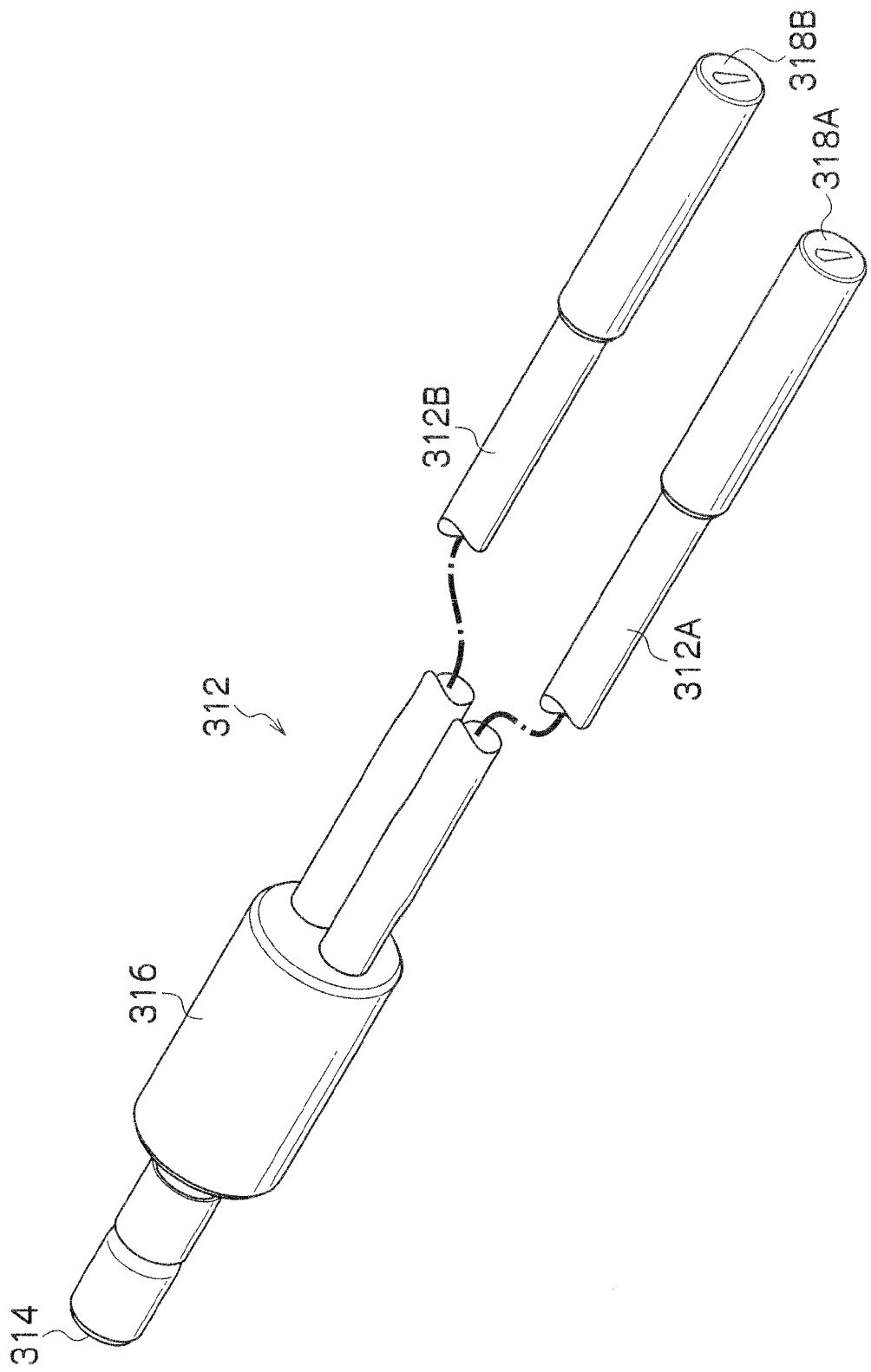
FIG. 29 is an oblique perspective view that illustrates a configuration example of an optic fiber that has a branched shape.
Figure 30:
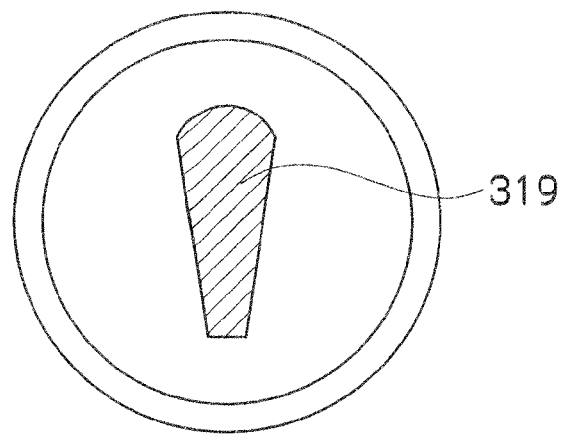
FIG. 30 is an enlarged view of a light exiting end face of the optic fiber shown in FIG. 29.

FIG. 29 is an oblique perspective view of an optic fiber that is used for the present example. An optic fiber 312 that is used as a light guide comprises a bundle of multiple small-diameter fiber element wires and a light exiting end face that is formed in a predetermined shape. Although an end 314 of the optic fiber 312 is tied in a single bundle, the optic fiber 312 branches into two paths at a midway point. Fiber bundles (designated by reference numerals 312A and 312B) produced by dividing the optic fiber 312 in two at a branch part 316 are bundles that comprises the same number of wires (one half of the total number of wires) as each other, and thus the light amount is divided in half. Further, the fiber bundle shape at the light exiting end faces 318A and 318B of the respective optic fibers 312A and 312B that have been branched forms an end face shape designated by reference numeral 319 (shaded part) in FIG. 30 so as to form a fan-shaped irradiation range on the disk surface.

Figure 31:
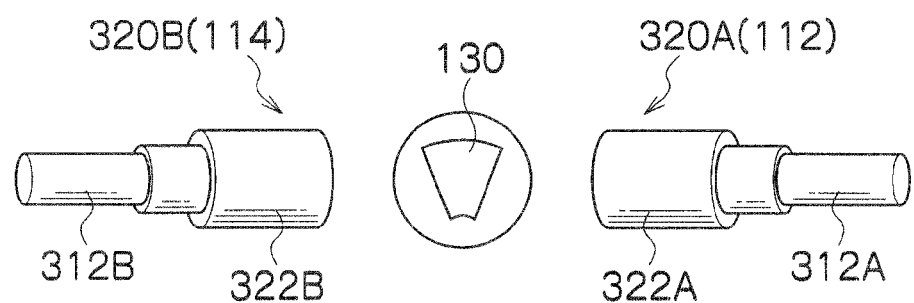
FIG. 31 shows views of the periphery of a light projecting part of an illumination apparatus as seen from a front face that is directly opposite a disk surface.
Figure 32:
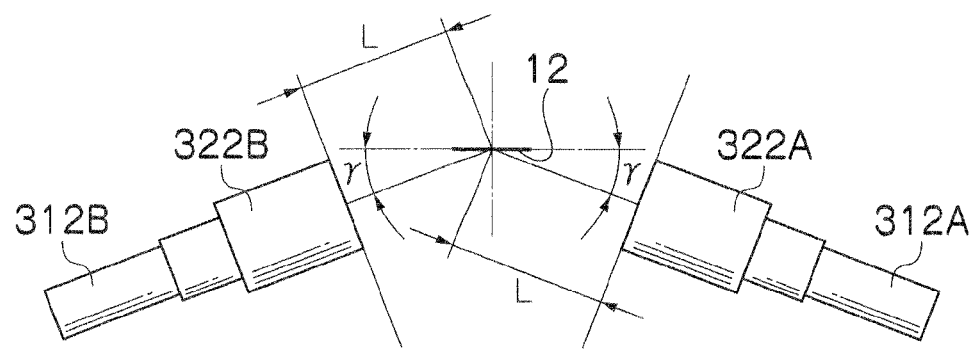
FIG. 32 is a plane view of FIG. 31.

FIG. 31 shows views of the periphery of light projecting parts of the illumination apparatus as seen from a front face that is directly opposite the disk surface, and FIG. 32 is a plane view thereof. In these drawings, the light projecting parts designated by reference numerals 320A and 320B are light projecting parts of the illumination apparatuses 112 and 114 shown in FIG. 28, respectively.

In FIG. 32, reference numerals 322A and 322B designate a lens. Each of the lenses 322A and 322B is mounted to the distal end of the optic fibers 312A and 312B, respectively. In this connection, the reference numerals 312A and 312B shown in FIGS. 31 and 32 correspond to reference numerals 132 and 134 described in FIG. 13A, respectively.

As shown in FIGS. 31 and 32, for the optic fibers 312A and 312B that are equipped with the lenses 322A and 322B, the irradiation distances and irradiation positions are adjusted and aligned so that the pattern illumination shapes overlap at approximately a focus position with respect to the shape of a fan-shaped portion (reference numeral 130) of an inspection region on the disk surface. At this time, by shifting the position of the lenses 322A and 322B slightly to a defocus position, the illumination of the fan-shaped inspection region is adjusted so as to irradiate an area that includes the entire inspection region and is also slightly wider than the inspection region. Since there is the problem that a pattern of unevenness in a fiber bundle is imprinted when the focus is placed on the disk surface, it is preferable to blur the focus by defocusing and decrease unevenness in the brightness. In this connection, by adjusting the relative positions of the distal ends of the fibers and the lenses 322A and 322B or adjusting the distance between the lenses 322A and 322B and the disk surface, the defocus amount at the disk surface can be adjusted.

Although a specific irradiation distance and the like is designed in accordance with various conditions such as the focal distances of lenses that are used, for example, a distance (irradiation distance L) from a distal end of a lens to the disk 12 that is the object for inspection is appropriately adjusted within a range of 50 to 100 mm.

Further, an angle γ formed between the disk surface and the irradiation optical axis of illumination light is preferably between 0 and 30 degrees, and according to the present example γ=20 degrees (angle of incidence is 70 degrees) (see FIG. 32). If an angle formed between the disk surface and the irradiation optical axis is greater than 30 degrees, imprinting of the illumination apparatuses 112 and 114 or directly reflected light is incident on the camera 102 (104). Accordingly, in order to accurately detect dust adhering to the disk 12, illumination at a shallow angle is preferable. Further, when an angle formed between the disk surface and the irradiation optical axis is 0 degrees or less, light is repelled by the disk 12 that is the object to be inspected and a shadow is formed, and it is thus not possible to cause dust to shine.

Figure 33:
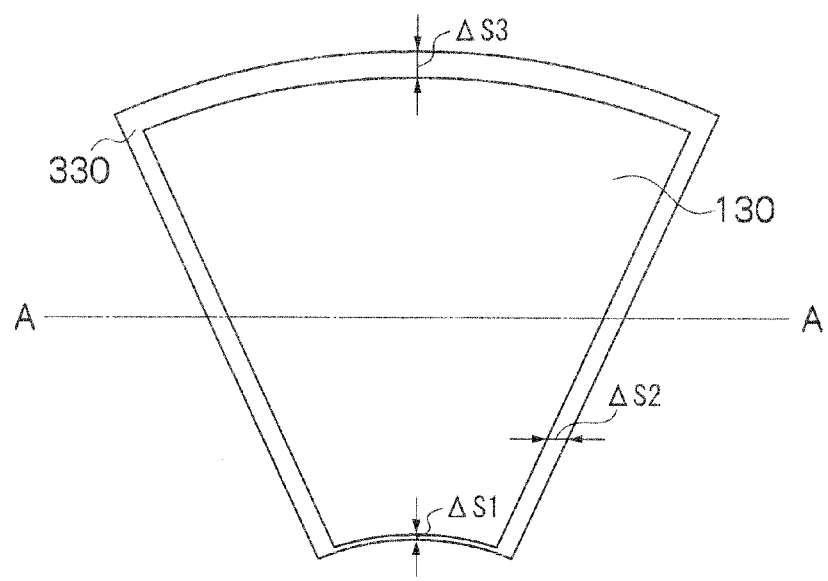
FIG. 33 is a view that shows the relation between a fan-shaped inspection region and an irradiation range of defocused pattern illumination.
Figure 34:
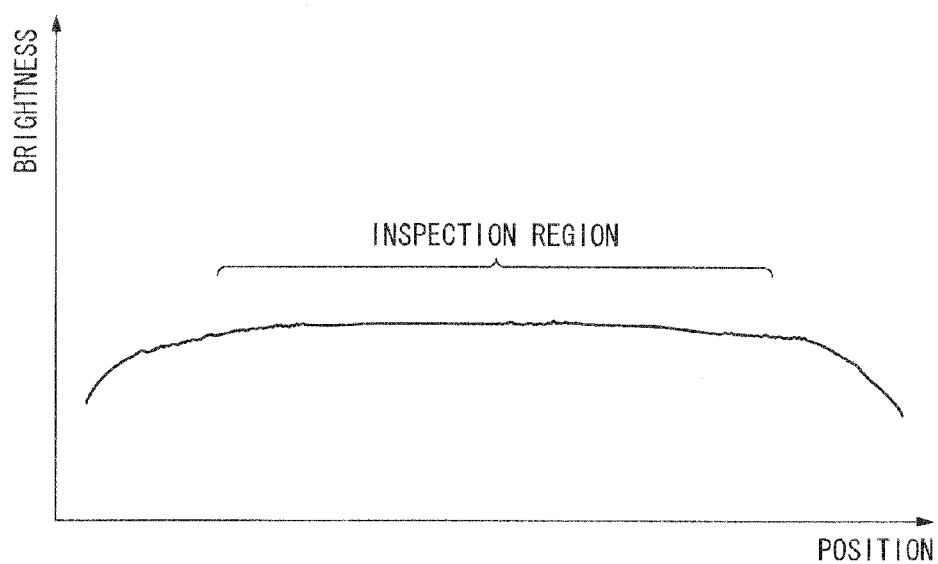
FIG. 34 is a graph that shows a luminance distribution along a straight line A-A shown in FIG. 33.

FIG. 33 is a view that describes the relationship between a fan-shaped inspection region and an irradiation range of defocused pattern illumination. As shown in FIG. 33, a pattern illumination irradiation range 330 is aligned so as to be wider than the fan-shaped inspection range 130. FIG. 34 is a view in which a luminance distribution on a straight line A-A in FIG. 33 is graphed. The abscissa represents position, and the axis of ordinates represents light amount (brightness). As shown in FIG. 34, although the brightness declines in an outer circumferential region (vicinity of boundary) of the pattern illumination, a range that is actually used for illuminating the inspection region is a center portion that is further on the inner side than the portion at which the brightness drops.

Thus, the configuration is such that a portion in which the brightness declines in an outer circumferential region of the fan-shaped pattern illumination light is not used, and furthermore, an image of an end face of a fiber bundle is blurred by defocusing to eliminate unevenness in brightness caused by imprinting of a fiber bundle. As a result, the brightness of the fan-shaped inspection region can be made uniform as much as possible.

In this connection, as the irradiation range of illumination light with respect to the inspection region widens, the problem of the influence caused by reflection of unwanted light on the inspection increases. Accordingly, it is desirable to adjust the size of the irradiation range of pattern illumination and the irradiation position in a range that is necessary and sufficient for ensuring uniformization of the brightness. In particular, in order to reduce to a minimum an unwanted reflection caused by claws 16, 17, and 18 of the chuck that grips the hole (inner circumference) in the center of the disk 12, as shown in FIG. 33, it is desirable that a protruding amount ΔS1 of illumination light in the inner circumferential edge direction is as small as possible. It is therefore desirable to make a protruding amount in the vertical direction small in comparison with a protruding amount ΔS2 of illumination light in a crosswise direction with respect to the inspection region or a protruding amount ΔS3 of illumination light in an outer circumferential edge direction (see FIG. 33).

Further, as described in FIG. 15, in order to reduce the influence of a reflection produced by the texture of the front surface of the disk, the occurrence of scattered light that is caused by the texture is suppressed by shining illumination light parallel to the texture of the front surface of the disk inside the inspection region.

Figure 35:
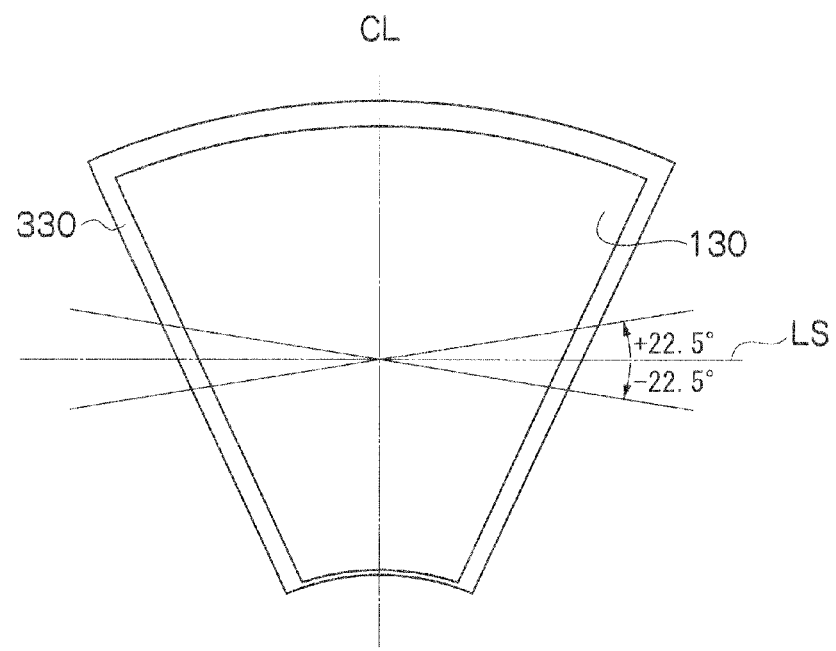
FIG. 35 is an explanatory view of an optical axis of an illumination light that is parallel to a texture direction.

According to FIGS. 31 and 32, although illumination light is shone parallel to (from the horizontal direction) a line that intersects at a right angle with a fan-shaped, bilaterally symmetrical center line of the inspection region, as shown in FIG. 35, by shining illumination light in a range of ±22.5 degrees on the basis of a line LS that intersects at a right angle with a fan-shaped, bilaterally symmetrical center line CL of the inspection region, the illumination light optical axis and the texture direction (concentric circles) of the inspection region will definitely be parallel somewhere. Hence, the illumination light is suitably adjusted in the range of ±22.5 degrees with respect to the base line LS.

Figure 36:
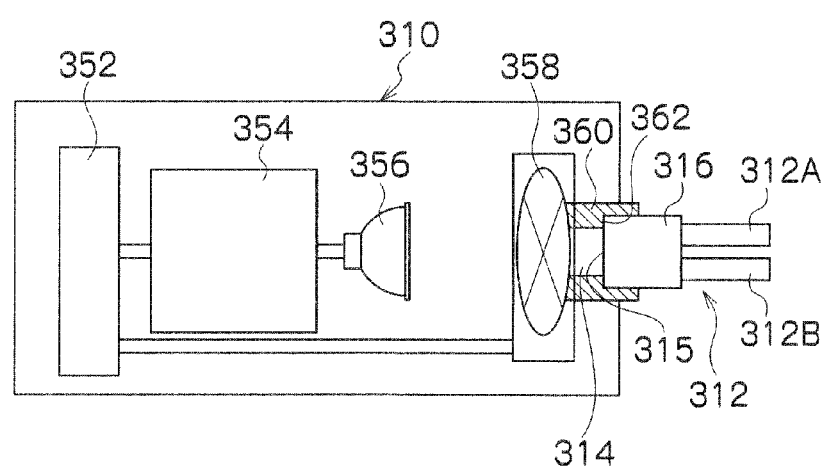
FIG. 36 is a configuration diagram of a light source apparatus that has a built-in shutter.

FIG. 36 is a configuration diagram of a light source apparatus that uses the illumination optical system of the present example. As shown in FIG. 36, a light source apparatus 310 includes a control board 352, a power supply circuit 354, and a metal halide lamp 356. The light source apparatus 310 also has a built-in mechanical shutter 358, and can control opening and closing of the mechanical shutter 358 by means of an input signal from the outside.

An end 314 (incident side) of the optic fiber 312 is connected to the light source apparatus 310 via a fixing member 360. A reference surface 362 for positioning when fixing the optic fiber 312 is formed in the fixing member 360. The optic fiber 312 is positioned by causing a stepped surface 315 of the optic fiber 312 to come in contact with and engage with the reference surface 362.

The mechanical shutter 358 is disposed between the metal halide lamp 356 and an incident end face (light receiving part) of the optic fiber 312. It is possible to switch between entry of light and blocking of light to the optic fiber 312 by an opening/closing operation of the mechanical shutter 358.

The control board 352 includes an unshown control circuit, and receives input signals from outside to control opening/closing operations of the mechanical shutter 358 and also control "ON" (lighting) and "OFF" (extinction of light) of the power supply circuit 354.

As described with the flowcharts shown in FIGS. 25 and 26, by performing opening/closing of the mechanical shutter 358 of the corresponding light source apparatus 310 in synchrony with the timing of imaging of surfaces to be inspected alternately by the camera 102 (camera 1) and 104 (camera 2), it is possible, to block illumination of a non-inspection surface that exerts an adverse effect of an inspection. More specifically, "ON" and "OFF" of the illuminations 1 and 2 as described in the flowcharts of FIGS. 25 and 26 is implemented by "opening" and "closing" of the mechanical shutter 358. Compared to controlling "on" (lighting) and "off" (extinction of light) of the metal halide lamp 356 itself, better responsiveness is obtained by controlling opening and closing of the shutter while maintaining the lighting state of the lamp, and this is also favorable in terms of stabilizing the light amount.

According to the illumination optical system of the present embodiment, it is possible to eliminate direct reflected light and high-order reflected light that act as interference. Further, by using a single light source apparatus 310 for one inspection surface of the two sides of the disk 12 and adopting a configuration in which illumination light is shone from plural courses using the optic fiber 312 that has a branched shape from the single light source apparatus 310, stabilization of the light amount balance can be maintained. If a case is supposed in which a single light source apparatus (lamp) is used for each light projecting part, the balance is liable to be lost due to light amount changes in each light projecting part caused by deterioration of the lamps and the like. With respect to this point, by adopting a configuration as in the present example in which a plurality of light projecting parts branch from a single light source apparatus, the light emitted from each light projecting part of the branched fibers decreases equally due to deterioration of the lamp, and hence the balance is maintained. Further, uniformization of a light amount can be realized by stabilization of the unevenness in brightness of illumination light in the inspection range 130.

In this connection, although according to the above described embodiment a configuration is exemplified in which an illumination light from a single light source apparatus 310 is branched into two parts by an optic fiber 312 and emitted from the left and right direction, a configuration is also possible that performs branching into an even greater number of parts from the single light source apparatus 310, and illumination light may be emitted from three or more directions with respect to a single inspection region. Furthermore, a configuration can also be adopted which performs illumination of both the front surface and the rear surface of the disk 12 using a single light source apparatus. In this case, respective fibers for front surface illumination and for rear surface illumination are branched from a single light source apparatus.

The inspection step performed by the disk inspection apparatus 100 according to the present embodiment is, for example, performed prior to a magnetic transfer step for recording servo information such as a servo signal for track positioning, an address information signal of the track, and a regenerative clock signal and the like on a magnetic disk of a hard disk apparatus.

The magnetic transfer step is a method that by applying a magnetic field for transfer in a state in which a master disk (transfer source disk) that carries transfer information by means of a minute concavo-convex pattern of a magnetic body and a slave disk (element to be transferred to) that has a magnetization recording layer (magnetic layer) that receives a transfer are arranged in close contact, transfers from a master disk on which format information corresponding to a magnetization pattern of the master disk or address information thereof in one batch to the slave disk. If dust is adhered to the disk, a problem such as a transfer failure or the generation of flaws on the surface of the master disk or the like may occur.

Accordingly, it is desirable to inspect the slave disk prior to performing the transfer to check for the adherence of dust using the disk inspection apparatus of the present example, and to exclude a slave disk for which adherence of dust is confirmed by the inspection from the manufacturing process (only select disks that have passed inspection). Further, since the position and size of dust particles can be identified, it is also possible to perform cleaning that is focused on particular points and to thereby reutilize a disk. Further, if cleaning is performed immediately after inspection, re-inspection can also be easily performed.

Although according to the above described embodiment an example has been described that uses the chucking apparatus according to the present invention in an inspection step, use of the chucking apparatus according to the present invention is not limited to an inspection step, and the chucking apparatus can also be utilized in another step, such as a disk cleaning step. For example, when the chucking apparatus according to the present invention is utilized in a cleaning step, because a disk is held in a vertical posture, adherence of dust can be prevented, and cleaning of both sides of the disk can be easily performed. Examples of a cleaning method in this case include an air flow or suction method, as well as a method of wiping with a nonwoven fabric or a head burnishing method that uses a head.

Naturally, the scope of application of the present invention is not limited to the above described example, and the present invention can be applied to various fields irrespective of the kind of disk.

Further, although a system configuration (FIG. 16) that uses a computer (PC) is exemplified according to the above described embodiment, when implementing the present invention a configuration can also be adopted that performs control by means of a program of inspection functions that is stored in a ROM (Read Only Memory) or the like using a microcomputer.

[Additional Notes]

The present specification includes the disclosure of inventions of the chucking apparatuses described hereunder that are suitable as a disk holding device.

(Invention 1): A chucking apparatus that holds a disk in which a hole is formed in a center part, the chucking apparatus having a plurality of claws that are inserted into a hole formed in a disk that is a holding object, and an urging device that urges at least one of the plurality of claws towards an outer side of the hole into which the plurality of claws are inserted; wherein the disk is held in a vertical posture by an outer circumferential part of the plurality of claws being pressurized into contact with a circumferential edge of the hole of the disk by the urging device.

According to invention 1, since a disk is held in a vertical posture by the outer circumferential part of the claws contacting against an inside edge of the disk, it is possible to perform simultaneous inspection of both sides of the disk without having to turnover (invert) the disk. It is also possible to avoid the adherence of particles due to gravity. Further, a down flow of clean air is not disturbed, and the level of cleanliness in the vicinity of the disk can be maintained.

(Invention 2): The chucking apparatus according to invention 1, wherein an outer diameter of a chuck main body to which the plurality of claws are attached is smaller than a hole diameter of the disk.

According to this configuration, when a disk surface is viewed from a perpendicular direction when the disk is in a chucked state, since the chuck main body is accommodated inside the hole of the disk, observation (inspection) can be performed as far as the vicinity of an inner circumferential edge with respect to both sides of the disk without a shadow being formed.

(Invention 3): The chucking apparatus according to invention 1 or 2, wherein the chuck main body to which the plurality of claws are attached is fixed to a spindle, and can rotate a disk that is held in the vertical posture.

According to this configuration, the entire surface of a disk can be inspected while rotating the disk.

(Invention 4): The chucking apparatus according to any one of inventions 1 to 3, wherein at least one of the plurality of claws is attached through a movable mechanism that is movable towards an inner side of the hole into which the plurality of claws are inserted.

In this case, it is desirable that a sliding portion of the movable mechanism is provided at a position that is separated by a distance equal to (outer circumferential radius—inner circumferential radius) of the disk or more from the disk that is held by the pressurized contact, and it is more desirable that the sliding portion of the movable mechanism is provided at a position that is separated a distance equal to the outer circumferential radius or more. Thereby, adherence to the disk of particles generated from the sliding portion can be suppressed.

(Invention 5): The chucking apparatus according to invention 4, wherein a sliding portion of the movable mechanism is provided at a position that is separated by a distance equal to (outer circumferential radius—inner circumferential radius) of the disk or more from the disk that is held by the pressurized contact.

(Invention 6): The chucking apparatus according to any one of inventions 1 to 5, wherein the urging device is a passive spring.

As a device that applies a chucking urging force, a configuration in which a passive spring of metal, resin, air, magnetism or the like is contained inside a chuck main body is preferable. According to this configuration, a disk can be held without applying a force from outside.

(Invention 7): The chucking apparatus according to any one of inventions 1 to 6, further comprising a claw driving device which moves at least one of the plurality of claws against an urging force of the urging device towards an inner side of the hole into which the plurality of claws are inserted, wherein, at a time of insertion of the plurality of claws into the hole, or when releasing the pressurized contact, at least one of the plurality of claws is moved towards an inner side of the hole by the claw driving device.

(Invention 8): The chucking apparatus according to invention 7, wherein the claw driving device is provided at an external part that is separated from the chuck main body to which the plurality of claws are attached.

(Invention 9): The chucking apparatus according to any one of inventions 1 to 8, wherein the claws are made with polybenzimidazole.

Polybenzimidazole exhibits a high level of abrasion resistance and slidability, and thus the generation of particles can be suppressed. Further, since polybenzimidazole has low reflectivity with no additives, adverse affects (imprinting or the like) on an optical inspection can be avoided. In this connection, although polyimide and polyimide-amide also exhibit a high level of abrasion resistance, carbon addition is required to achieve slidability and low reflectivity, and in some cases there is an increase in particles.

(Invention 10): The chucking apparatus according to any one of inventions 1 to 9, wherein the claws have an arc-shaped outer circumferential part that corresponds to a circumferential edge of a hole of the disk, and hold the disk by only contacting against a circumferential edge of the hole of the disk, without contacting a flat portion on both sides of the disk in a state in which the disk is being held.

According to this configuration, adherence of particles to a disk surface (flat portion) is suppressed, and inspection of almost the entire flat portion is enabled.

(Invention 11): The chucking apparatus according to any one of inventions 1 to 10, wherein as the plurality of claws, two fixed claws and one movable claw are arranged on the same circumference, and an angle between positions of the two fixed claws around the center is smaller than an angle between a position of the movable claw and a position of the fixed claw around the center.

(Invention 12): The chucking apparatus according to invention 11, wherein when mounting a disk to the chucking apparatus or when de-mounting a disk from the chucking apparatus, the two fixed claws are positioned at the same height and the movable claw is positioned at a lower position than the two fixed claws.

According to this configuration, the stability of disk holding can be improved, and it is also possible to suppress occurrence of flaws or particles due to abrasion at a time of chucking.

What is claimed is:
1. A hard disk inspection apparatus, comprising:
a disk holding device which holds a hard disk;
a light source which generates a light that illuminates an inspection region portion of a hard disk that is held by the disk holding device;
a plurality of light projecting parts which irradiate the inspection region portion with the light;

a light guide which has a branched shape and guides a light from the light source to the plurality of light projecting parts; and an image pickup device which takes an image by receiving reflected light from the inspection region portion;

wherein an illumination light is shone onto the inspection region from plural courses by shining the illumination light that is guided by the light guide onto the inspection region from the plurality of light projecting parts.

2. The hard disk inspection apparatus according to claim 1, wherein the light source and the light guide are provided for each of a first inspection surface that is a surface of one side of the hard disk and a second inspection surface that is a surface of another side of the hard disk.

3. The hard disk inspection apparatus according to claim 1, wherein:

the light projecting parts irradiate an inspection region portion which has a predetermined shape and is located on the hard disk including an edge of the hard disk, with the illumination light which has a shape that is approximately the same as the shape of the inspection region portion.

4. The hard disk inspection apparatus according to claim 2, wherein:

the light projecting parts irradiate an inspection region portion which has a predetermined shape and is located on the hard disk including an edge of the hard disk, with the illumination light which has a shape that is approximately the same as the shape of the inspection region portion.

* * * * *